United States Patent [19]

Kishi

[11] Patent Number: 4,536,336
[45] Date of Patent: Aug. 20, 1985

[54] NEW ANTHRACYCLINONES AND THEIR PRODUCTION

[75] Inventor: Yoshito Kishi, Belmond, Mass.

[73] Assignee: Meiji Seika Kaisha, Ltd., Kyobashi, Japan

[21] Appl. No.: 565,216

[22] Filed: Dec. 23, 1983

[30] Foreign Application Priority Data

Dec. 23, 1982 [JP] Japan ................... 57-225089

[51] Int. Cl.³ .............. C07C 50/36; C07C 49/76; C07C 49/74
[52] U.S. Cl. ...................... 260/351.1; 260/351.5; 260/365; 260/376; 260/383
[58] Field of Search .............. 260/351.1, 351.5, 365, 260/376, 383; 549/457, 494

[56] References Cited

U.S. PATENT DOCUMENTS

| 4,012,448 | 3/1979 | Smith et al. | 260/365 |
| 4,147,706 | 4/1979 | Kende et al. | 260/376 |
| 4,329,339 | 5/1982 | Fujiwara et al. | 260/365 |
| 4,415,498 | 11/1983 | Anathasabramanian et al. | 260/351.1 |

FOREIGN PATENT DOCUMENTS 0113566  7/1984  European Pat. Off. ......... 260/351.1

Primary Examiner—Richard L. Raymond
Assistant Examiner—Raymond Covington
Attorney, Agent, or Firm—Larson and Taylor

[57] ABSTRACT

A new compound of the formula

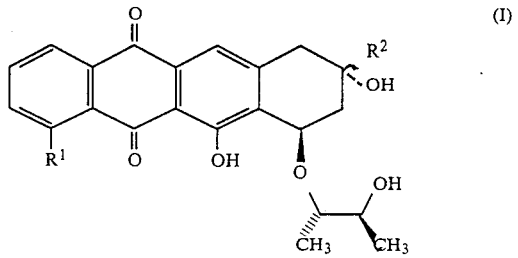

wherein $R^1$ is a hydrogen atom, a hydroxyl group or an alkoxyl group of 1-4 carbon atoms and $R^2$ is an ethyl group or acetyl group is now provided, which is an intermediate compound useful for synthesis of antitumor anthracyclines. This new anthracycline is produced by cyclization of a new compound of the formula

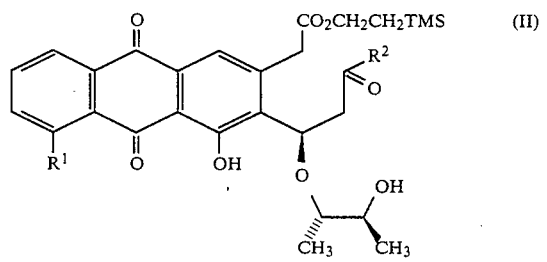

wherein $R^1$ is as defined above and TMS denotes a trimethylsilyl group, followed by decarboxylation of the cyclization product.

14 Claims, No Drawings

NEW ANTHRACYCLINONES AND THEIR PRODUCTION

SUMMARY OF THE INVENTION

This invention relates to a new anthracycline compound and also to a process for the production of this new compound.

BACKGROUND OF THE INVENTION

Anthracycline antibiotics are useful as antitumor agent and are generally produced by fermentation. For low cost production of anthracyclines, syntheses of the aglycone moiety of the anthracycline compound, anthracyclinone, has also been attempted (see Arcamone "Topics in Antibiotic Chemistry" Vol. 2, pages 99–239 (1978) and Terashima "Journal of Synthetic Organic Chemistry, Japan" 40, 20 (1982)).

The present inventor has now found that when a naphthoquinone or juglone and a furan diene compound of the formula (III) shown later are employed as the starting material and condensed, the regiospecific Diels-Alder condensation readily proceeds, that the adduct product so obtained from the Diels-Alder reaction can be converted into an acetal compound by the reaction with L-(+)-2,3-butanediol, and that when this acetal compound is condensed with 1-(trimethylsilyl)-2-butanone or 3-methyl-1-(trimethylsilyl)-3-butene-2-on, followed by cyclization of the resultant aldol condensation product, the anthracyclinone skelton can be constructed under stereochemical control. Thus, the present inventor has now first succeeded in achieving practical asymmetric syntheses of the new anthracycline compound of the formula (I) and also anthracyclinone of formula (A) shown below. On the basis of these new findings, this invention has been accomplished.

DETAILED DESCRIPTION OF THE INVENTION

According to a first aspect of this invention, therefore, there is provided, as the new compound useful as an intermediate for synthesis of antitumor anthracyclines, a compound represented by the general formula (I)

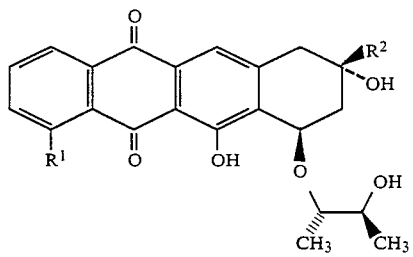

wherein $R^1$ denotes a hydrogen atom, a hydroxyl group or an alkoxyl group of 1–4 carbon atoms and $R^2$ denotes an ethyl group or an acetyl group.

According to a second aspect of this invention, there is provided a process for the production of the compound of the general formula

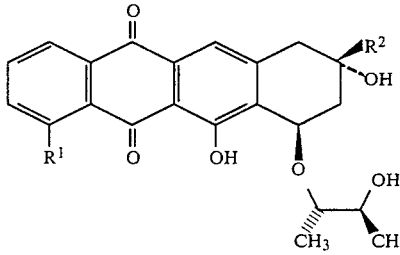

wherein $R^1$ and $R^2$ are as defined above, which comprises the steps of:

(a) cyclizing the compound of the formula

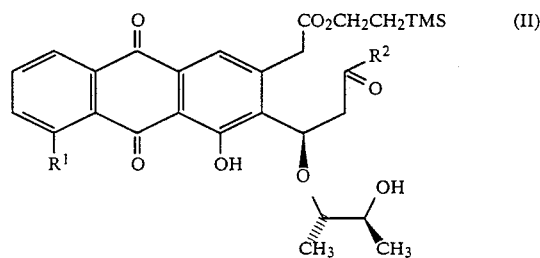

wherein $R^1$ and $R^2$ are as defined above and TMS denotes a trimethylsilyl group by treating with a base in an organic solvent to produce the compound of the formula

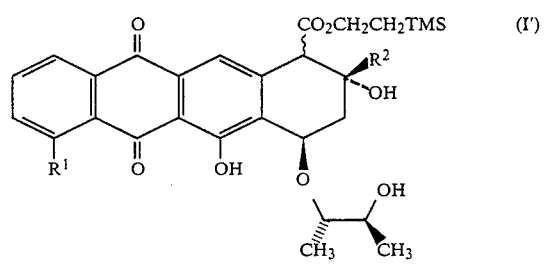

wherein $R^1$, $R^2$ and TMS are as defined above, and (bi) decarboxylating the compound of the formula (I') by treating with a tetra-alkyl ammonium fluoride or hydrogen fluoride in an organic solvent to produce the desired compound of the formula (I).

According to a third aspect of this invention, there is provided a process for the production of the compound of the formula (I)

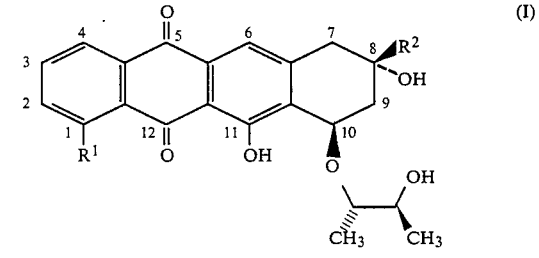

wherein $R^1$ and $R^2$ are as defined above, which comprises the consecutive steps of:

(i) subjecting a compound of the formula (III)

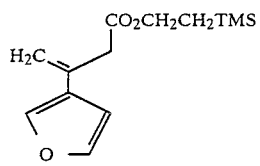

(III)

wherein TMS denotes a trimethylsilyl group, and a compound of the formula (IV)

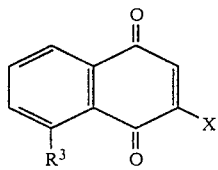

(IV)

wherein $R^3$ is a hydrogen atom or a hydroxyl group and X is a bromo group or a hydrogen atom to Diels-Alder condensation either in the presence of 4,4'-thiobis(6-t-butyl-3-methylphenol) as a radical scavenger and an acid acceptor when the group X of the compound (IV) denotes a bromo group, or in the presence of a catalyst when the group X of the compound (IV) denotes a hydrogen atom, to produce the compound of the formula (Va)

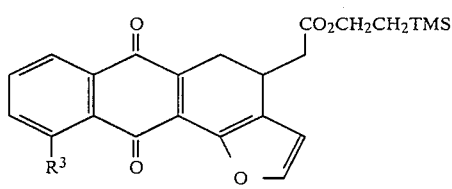

(Va)

wherein $R^3$ and TMS are as defined above, (ii) oxidizing the compound of the formula (Va) in the presence of a base to produce the compound of the formula (V)

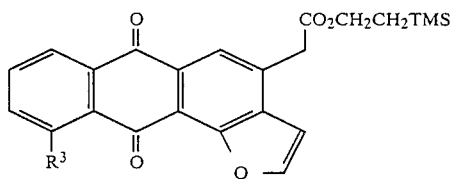

(V)

wherein $R^3$ and TMS are as defined above, (iii) optionally alkylating the group ($R^3$) of the compound of the formula (V) where $R^3$ denotes a hydroxyl group, by reacting with an alkyl iodide of 1–4 carbon atoms in an organic solvent to produce the compound of the formula (VI)

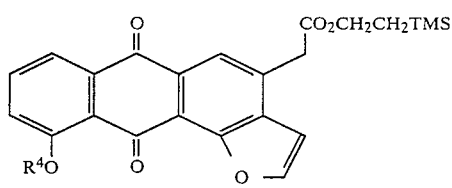

(VI)

wherein $R^4$ is an alkyl group of 1–4 carbon atoms and TMS is as defined above, (iv) ozonolyzing the compound of the formula (VIa)

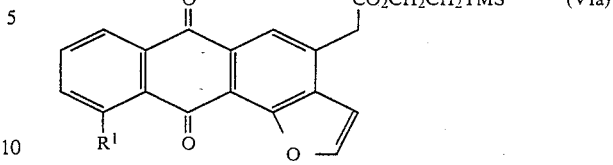

(VIa)

wherein $R^1$ is a hydrogen atom, a hydroxyl group or an alkoxyl group of 1–4 carbon atoms as defined above and TMS is as defined above [the compound of the formula (VIa) generically representing both the compound of the above formula (V) and the compound of the above formula (VI)], thereby to give the aldehyde compound of the formula (VIb)

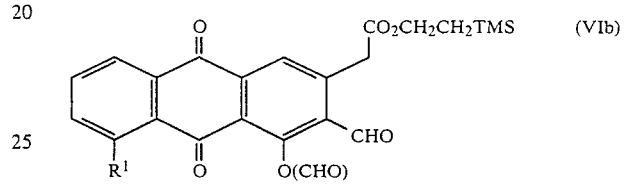

(VIb)

wherein $R^1$ and TMS are as defined above, (v) reacting the aldehyde compound of the formula (VIb) with L-(+)-2,3-butanediol in an inert organic solvent in the presence of an acid catalyst to produce an acetal compound of the formula (VII)

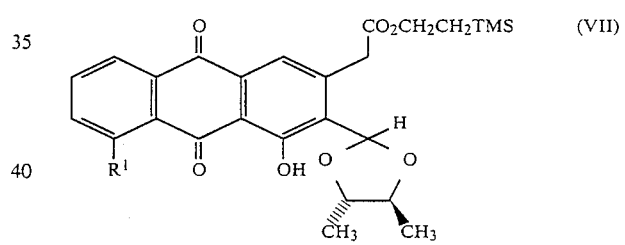

(VII)

wherein $R^1$ and TMS are as defined above, (vi) either condensing the acetal compound of the formula (VII) and 1-(trimethylsilyl)-2-butanone of the formula (VIII)

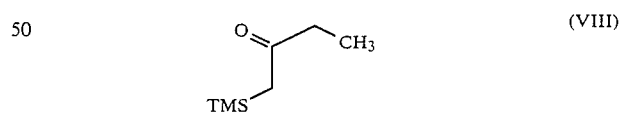

(VIII)

wherein TMS is a trimethylsilyl group to produce a compound of the formula (II')

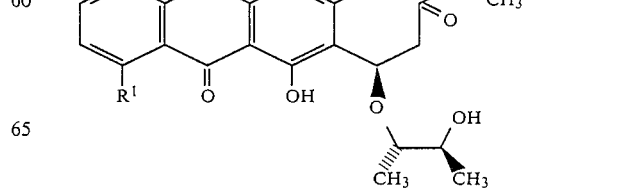

(II')

wherein R¹ and TMS are as defined above; or condensing the acetal compound of the formula (VII) and 3-methyl-1-(trimethylsilyl)-3-buten-2-on of the formula (IX)

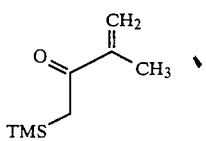
(IX)

wherein TMS is as defined above to produce a compound of the formula (II″)

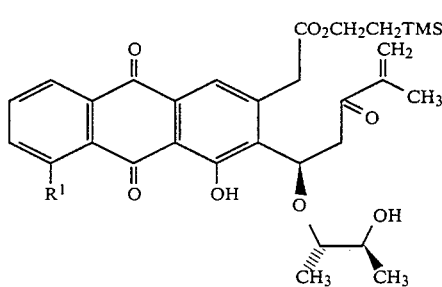
(II″)

wherein R¹ and TMS are as defined above, followed by ozonolyzing the compound of the formula (II″) to produce a compound of the formula (II‴)

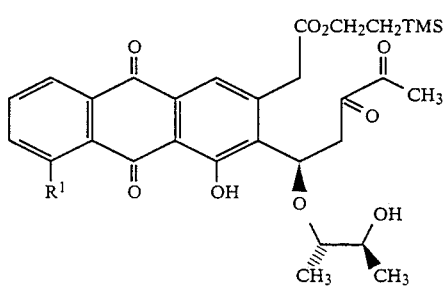
(II‴)

wherein R¹ and TMS are as defined above,
(vii) cyclizing a compound of the formula (II)

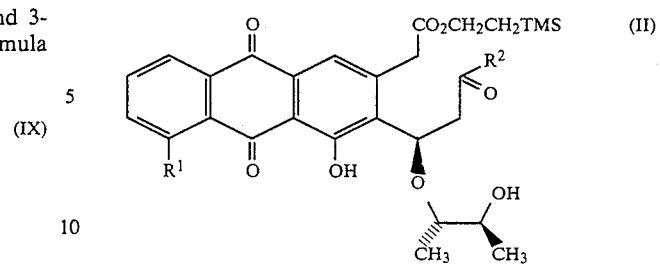
(II)

wherein R¹ is as defined above and R² is an ethyl group or an acetyl group [the compound of the formula (II) generically representing both the compound of the formula (II′) and the compound of the formula (II‴)] by the treatment with a base in an anhydrous organic solvent to produce a compound of the formula (I′)

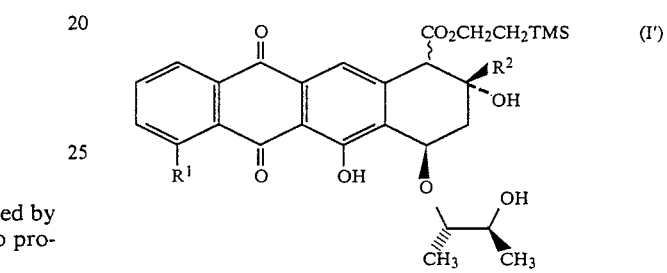
(I′)

wherein R¹, R² and TMS are as defined above, and
(viii) decarboxylating the cyclization product of the formula (I′) by treating with a tetraalkyl ammonium fluoride or hydrogen fluoride in an organic solvent to produce the desired compound of the formula (I).

The production of the new compound of the formula (I) of this invention by the process according to the third aspect of this invention is now depicted schematically by the following reaction scheme in which it is shown that the preparation of the compound of the formula (II) where R² denotes an ethyl group and the preparation of the compound of the formula (II) where R² denotes an acetyl group proceed in part through different routes via the different compounds of the formulae (II′) and (II‴).

REACTION SCHEME

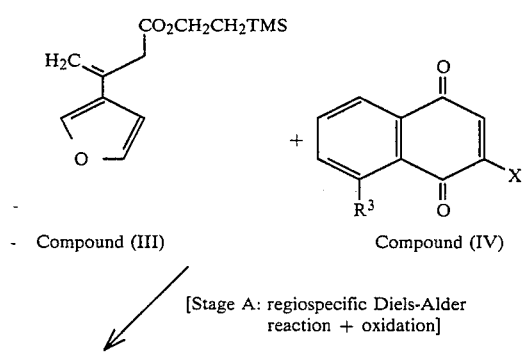

- Compound (III)        Compound (IV)

[Stage A: regiospecific Diels-Alder reaction + oxidation]

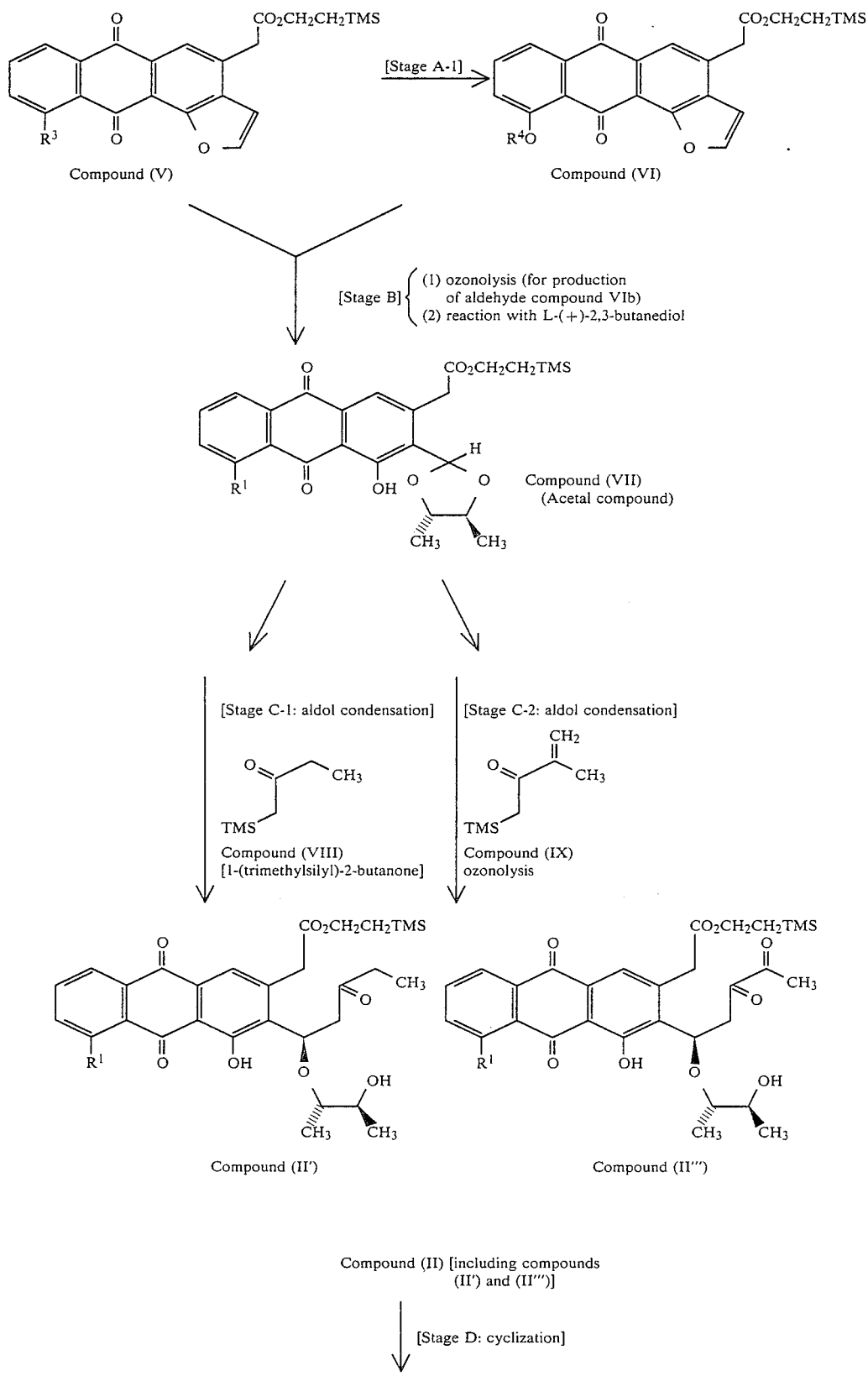

-continued
REACTION SCHEME

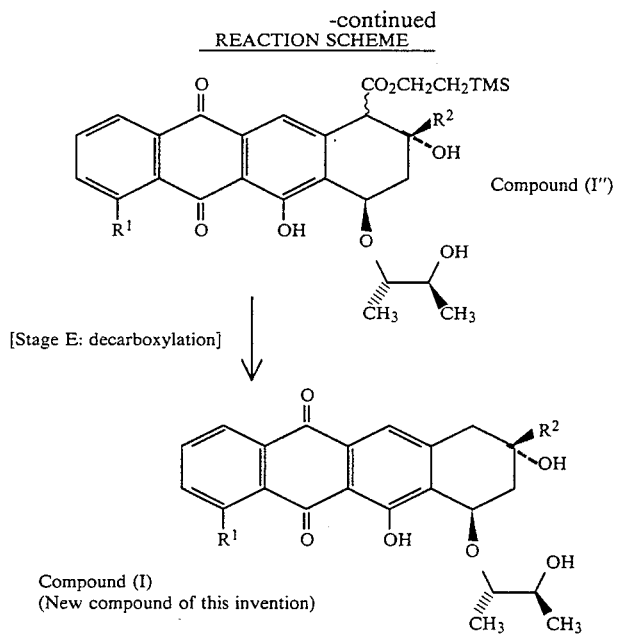

Compound (I″)

[Stage E: decarboxylation]

Compound (I)
(New compound of this invention)

In the above reaction scheme, the substituent $R^3$ denotes a hydrogen atom or a hydroxyl group, X denotes a hydrogen atom or a bromine atom, TMS denotes a trimethylsilyl group, $R^1$ denotes a hydrogen atom, a hydroxyl group or an alkoxyl group of 1–4 carbon atoms, $R^4$ denotes an alkyl group of 1–4 carbon atoms, and $R^2$ denotes an ethyl group or an acetyl group in the concerned compounds.

The new compound of the formula (I) according to this invention can be converted into an anthracyclinone compound of the formula (A)

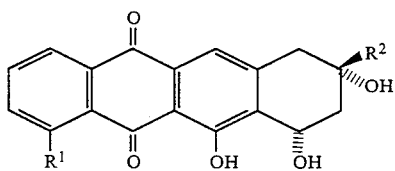

(A)

wherein $R^1$ and $R^2$ are as defined above, when it is treated with an acid, especially trifluoroacetic acid.

The process of this invention is now described in detail with reference to each stage shown in the above reaction scheme.

Stage A: In this stage, principally, the compound (III) is condensed with the naphthoquinone compound (IV) (corresponding to the step (i) of the third aspect process of this invention). The reaction conditions employed for this Diels-Alder reaction are depending on the nature of ths substituent X of the compound (IV) used as the starting material. Thus, when X is a bromo group in the compound (IV), the condensation of the compound (III) and the compound (IV) may be carried out under thermal conditions by heating at a refluxing temperature of the solvent employed. An inert organic solvent such as aromatic hydrocarbons, for example, benzene, toluene, xylene may suitably by employed in this reaction. The reaction is effected in the presence of an acid acceptor such as strontium carbonate for the purpose of preventing degradation of the reactants and in the presence of 4,4′-thiobis(6-t-butyl-3-methylphenol) as radical scavenger for causing the reaction to proceed smoothly.

When X is a hydrogen atom in the compound (IV), the reaction can be carried out not only under thermal condition by heating as described above but also can be effected under the radical cation condition. This reaction under the radical cation conditions may be carried out in an inert organic solvent at a reaction temperature of $-20°$ C. to $0°$ C. In order to promote the radical cation reaction, it is desirable that the reaction is effected in the presence of a catalyst such as tris(p-bromophenyl)ammoniumyl hexachloroantimonate [(p-$BrC_6H_4)_3N^+SbCl_6^-$].

By the Diels-Alder reaction, there is produced the compound of the formula

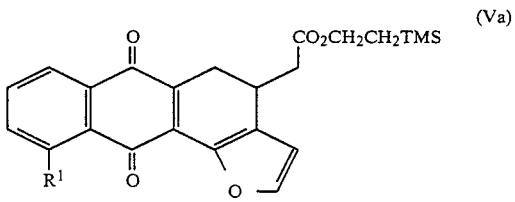

(Va)

wherein $R^1$ and TMS are as defined above. This compound may be employed in a next reaction step without purification.

After the end of the Diels-Alder condensation, the crude product so obtained containing the compound (Va) is then oxidized with air or oxygen gas in a second step (corresponding to the step (ii) of the third aspect process of this invention) in such a manner that the compound (Va) in solution in an inert organic solvent such as chloroform is treated with air or oxygen gas in the presence of a base, for example, an alkylamine, preferably di-isopropylethylamine. In this way, there is produced the compound of the formula (V) shown in the reaction scheme.

Stage A-1: In this stage, the alkylation is effected to convert the compound (V) where the substituent $R^3$ is a hydroxyl group, into the compound (VI) where the hydroxyl group has been replaced by an alkoxyl group.

The alkylation can be effected in by usual method in an organic solvent such as chloroform and dichloromethane using an alkyl iodide as the alkylating reagent and preferably in the presence of silver oxide as an acid acceptor (corresponding to the optional step (iii) of the third aspect process of this invention).

Stage B: In this stage, the compound (V) or the compound (VI) [generically represented by the compound of the formula (VIa) mentioned before in respect of the third aspect process of this invention] is firstly ozonolyzed (corresponding to the step (iv) of the third aspect process of this invention) to produce an aldehyde compound of the formula

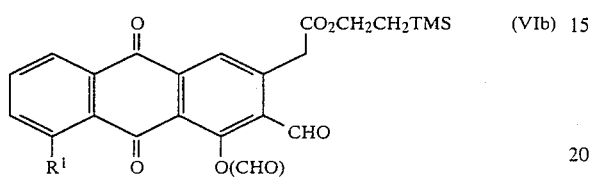 (VIb)

wherein $R^1$ and TMS are as defined above. The ozonolysis of the compound (V) can be carried out by passage of ozone gas through a solution of the compound (V) in an organic solvent such as halogenated hydrocarbons, preferably methylene chloride, chloroform, carbon tetrachloride and the like at a low temperature, preferably in the vicinity of −78° C. After the ozonolysis was completed, the reaction mixture can be treated in an usual manner, for example, by purging with nitrogen, so that the excess of ozone can be removed from the reaction mixture. The aldehyde product so obtained can be utilized as such in a next step without purification.

In the next step, the aldehyde compound (VIb) is reacted with L-(+)-2,3-butanediol to produce the acetal compound (VII) (corresponding to the step (v) of the third aspect process of this invention).

The reaction of the aldehyde compound (VIb) with the butanediol can be carried out by refluxing a mixture of the aldehyde compound and the butanediol in an inert organic solvent such as dry toluene under stream of an unreactive gas such as nitrogen gas, argon gas and the like. The reaction may suitably be effected in the presence of an acid catalyst such as pyridinium p-toluenesulfonate and the like. The acetal compound (VII) so obtained can be isolated from the reaction mixture by chromatography and then purified by recrystallization from methanol. The acetal compound (VII) is usually obtained as yellow-colored needles.

In a further step, the acetal compound (VII) is condensed with a (trimethylsilyl)methylketone compound of the formula (VIII) or (IX). This aldol condensation step is necessary to be effected using different procedures and different reaction conditions, dependently upon the nature of the substituent $R^2$ which is to be provided in the final compound (I) of this invention, as described below in more details.

Stage C-1: When the substituent $R^2$ of the final product (I) of this invention is to be ethyl, the aldol condensation step of reacting the acetal compound (VII) with 1-(trimethylsilyl)-2-butanone [$(CH_3)_3Si—CH_2—CO—CH_2CH_3$], that is, the compound (VIII) is effected as said further step (corresponding to a first alternative procedure of the step (vi) of the third aspect process of this invention) to produce the compound (II'). This reaction can be carried out in an anhydrous organic solvent such as dry acetonitrile, tetrahydrofuran (THF) and the like at a low temperature from −20° C. to −13° C. and in the presence of a Lewis acid such as tin tetrachloride as catalyst. The reaction may suitably be carried out under stream of an unreactive gas such as argon in order to prevent degradation of the reactants.

In this aldol condensation reaction, there is by-formed, in addition to the desired compound (II'), some quantity of its stereo isomer of the formula

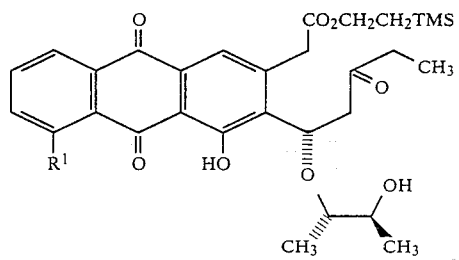

wherein $R^1$ and TMS are as defined above. For isolation and purification of the desired compound (II'), therefore, the aldol condensation products may be chromatographed on silica gel developed with chloroform-ethyl acetate as eluent, followed by recrystallization from hexane, affording the compound (II') as desired.

Stage C-2: When the substituent $R^2$ of the final product (I) is to be acetyl, the aldol condensation step of reacting the acetal compound (VII) with 3-methyl-1-(trimethylsilyl)-3-buten-2-on, that is, the compound (IX) is effected as said further step (corresponding to a second alternative procedure of the step (vi) of the third aspect process of this invention) to produce the compound (II''). This reaction can be carried out in an organic solvent such as toluene, acetonitrile, THF and the like at a low temperature, preferably in the vicinity of −78° C. and generally at a temperature of −30° C. to −80° C. and in the presence of a Lewis acid such as boron trifluoride and the like as catalyst.

This aldol condensation reaction gives the compound of the formula

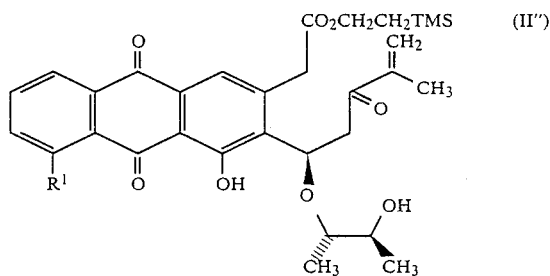 (II'')

wherein $R^1$ and TMS are as defined above, together with its stereo isomer of the formula.

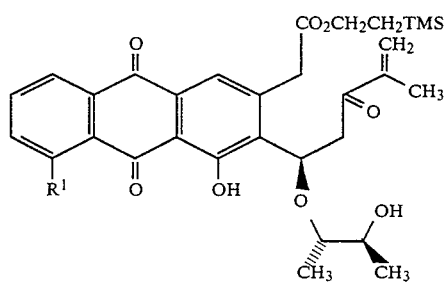

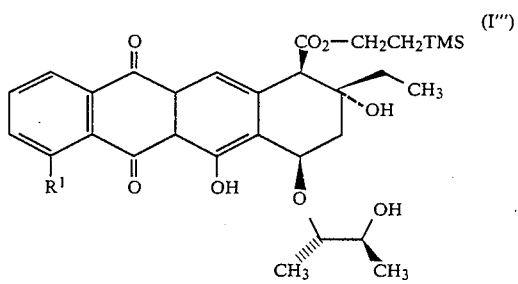

wherein $R^1$ and TMS are as defined above. The resulting aldol condensation products comprising the compound (II″) and its stereo isomer in mixture may be used as such in the next, ozonolysis step without separation of the compound (II″) from its isomer.

The above-mentioned aldol condensation step for producing the compound (II″) is followed by a step of ozonolyzing this compound in an organic solvent such as methanol, dichloromethane and the like at a low temperature, preferably of −78° C. so that the compound of the formula (II‴) shown in the reaction scheme is formed. For this purpose, ozone gas may conveniently by passed into a solution of the compound (II″) in an appropriate solvent. The reaction solution is then treated in an usual manner, for example, by purging with nitrogen gas, so that the excess of ozone is removed therefrom. The reaction solution is then evaporated in vacuo to give the residue containing the compound (II‴) which may then be isolated and purified by chromatography on silica gel developed with benzene-ethyl acetate as eluent, affording the compound (II‴), usually as a yellow syrup.

The compounds of the formula (II′) and the compound of the formula (II‴) obtained as above are new compounds which are not described in any printed publications.

Stage D: In this stage, the compound (II′) or the compound (II‴) produced as above (generically represented by the compound (II) shown hereinbefore in respect of the second or third aspect process of this invention) is cyclized (corresponding to the step (a) of the second aspect process or to the step (vii) of the third aspect process of this invention). For this purpose, the cyclization reaction may be carried out by treating the compound (II) with a base such as DBN (namely, 1,5-diazabicyclo-[4.3.0]nonene-5) or DBU (namely, [1.8]diazabicyclo-[5.4.0]undec-7-ene) in an anhydrous organic solvent such as dry THF at ambient temperature. This reaction may desirably be effected under stream of nitrogen gas in order to prevent degradation of the cyclization product. By this cyclization, there is formed the compound of the formula (I″) shown in the reaction scheme.

In this cyclization step, there is by-formed, in addition of the compound (I″), its stereo isomer of the formula wherein $R^1$ and TMS are as defined above,. The compound (I″) may be isolated from its stereo isomer (I‴) by chromatography on silica gel developed with benzene-ethyl acetate (5:2), if necessary. If desired, however, the products from this cyclization step may be used as such in the next, decarboxylation step without separation of the compound (I″) from the compound (I‴).

Stage E: In this stage, the compound (I′) [including the compounds (I″) and (I‴)] produced as above is decarboxylated to remove the (trimethylsilyl)ethoxycarbonyl group (—CO₂CH₂CH₂TMS) (corresponding to the step (b) of the second aspect process or to the step (viii) of the third aspect process of this invention). This decarboxylation reaction may be carried out by treating the compound (I′) with a solution of a tetraalkyl ammonium fluoride, especially tetra-n-butyl ammonium fluoride or hydrogen fluoride in an inert organic solvent such as dry THF or DMF at ambient temperature or a low temperature. This reaction may suitably be carried out under stream of nitrogen gas in order to prevent degradation of the decarboxylated product. By this reaction, there is produced the desired compound of the formula (I) shown in the reaction scheme.

The new compound (I) produced as above according to this invention can be converted into an anthracyclinone compound of the formula (A) shown hereinbefore when it is treated with an acid such as trifluoroacetic acid at a low temperature (see Examples 17–22 given later). When certain sugar moiety is condensed with the 7-position of the anthracyclinone compound (A) by a known method, the product obtained is potentially useful antibiotics having antitumor activity such as daunomycins.

In the process depicted in the foregoing reaction scheme, a naphthoquinone or juglone compound such as the compound (IV) is condensed with the diene compound (III) under the Diels-Alder reaction conditions (in Stage A of the reaction scheme), when the condensation reaction proceeds regiospecifically so that the diene compound (III) is combined in the resultant condensation product in such direction as observed with the compound (V). Further, when the aldehyde compound (VIb) is reacted with L-(+)-2,3-butanediol (in Stage B of the reaction scheme), there is formed the acetal compound of the formula (VII). Furthermore, when this acetal compound (VII) is reacted with a silylketone (VIII) or (IX) such as ethyl (trimethylsilyl) methyl ketone (in Stage C-1 or C-2 of the reaction scheme), the aldol condensation takes place under a high stereochemical control to afford the compound having the desired chirality as shown by the formula (II′) or (II″). These facts are now firstly discovered by the present inventor. These new reactions are associated in an ingenious way to provide the new processes of this invention which achieved first practical asymmetric syntheses of anthracyclinones in a high optical purity.

The process of this invention is now illustrated with reference to Examples 1-4; Examples 5-6; Examples 7-8; Examples 9-10; Examples 11-14 and Examples 15-16.

EXAMPLE 1

Synthesis of 4-[2'-(trimethylsilyl)ethoxycarbonylmethyl]-8-hydroxy-anthraquinofuran The titled compound having formula (V') given below was synthesized through the following route which corresponds to Stage A of the reaction scheme hereinbefore shown.

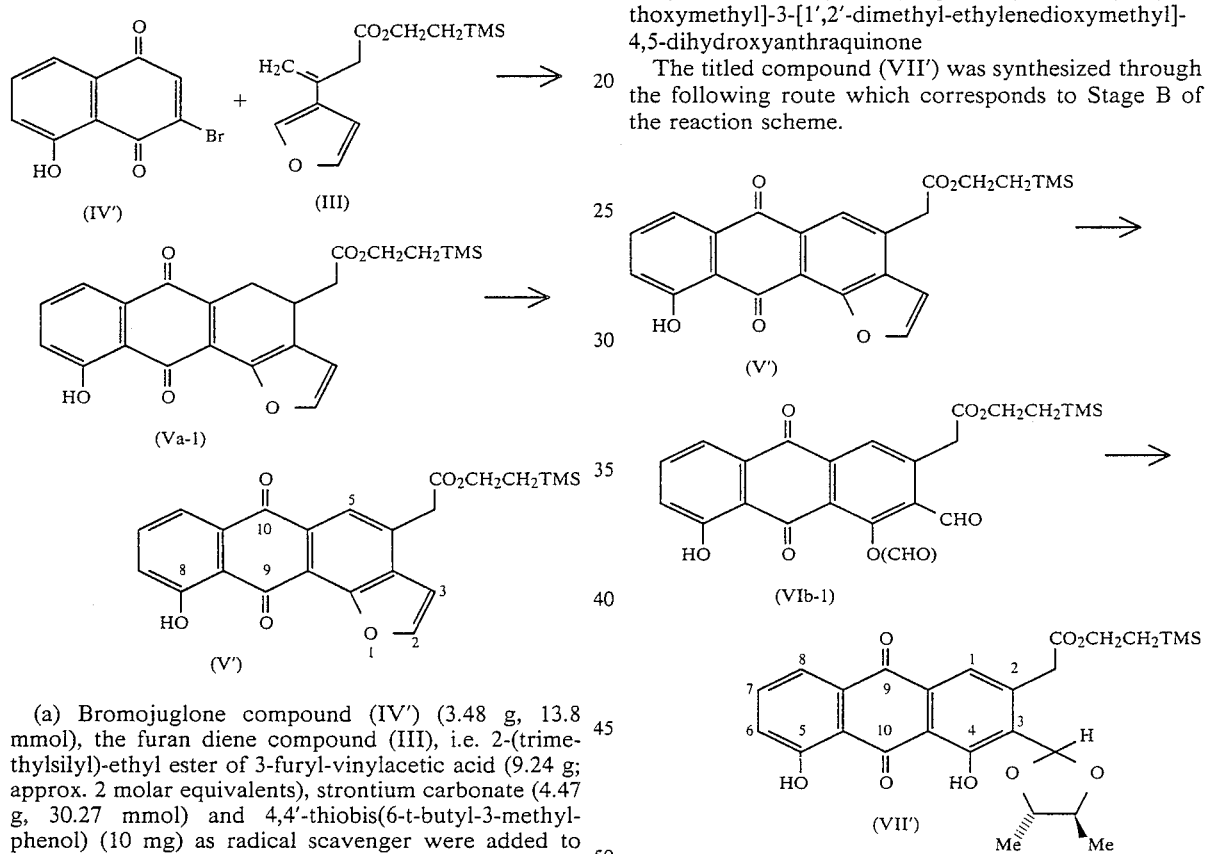

(a) Bromojuglone compound (IV') (3.48 g, 13.8 mmol), the furan diene compound (III), i.e. 2-(trimethylsilyl)-ethyl ester of 3-furyl-vinylacetic acid (9.24 g; approx. 2 molar equivalents), strontium carbonate (4.47 g, 30.27 mmol) and 4,4'-thiobis(6-t-butyl-3-methylphenol) (10 mg) as radical scavenger were added to benzene (350 ml), and the mixture was refluxed under azeotropic distillation for 23 hours to effect Diels-Alder condensation (corresponding to the step (i) of the third aspect process of this invention).

The reaction solution was passed through a Celite bed to remove the precipitated inorganic salts. The Celite bed was then washed with methylene chloride. The reaction solution was combined with the methylene chloride washings and then concentrated in vacuo to leave a red-black residue. The residue was purified by silica gel column chromatography with elution first with benzene to elute the starting compound and then with benzene-ethyl acetate (95:5) to elute the product, i.e. compound (Va-1), which was separated as a red solid (44.1 g; 76%). This was used for the next step without purification.

(b) The crude dihydrobenzofuran compound (Va-1) so obtained (4.22 g, 10 mmol) and diisopropylethylamine (3.47 ml, 20 mmol) were added to chloroform (347 ml), and the mixture was stirred at room temperature for 17 hours to effect air-oxidation (corresponding to the step (ii) of the third aspect process of this invention) and then concentrated in vacuo to leave yellow-black residue. The residue was dissolved in chloroform and the solution was chromatographed in silica gel column (silica gel G: 300 ml) with elution first with chloroform and then with benzene-ethyl acetate (3:2) to yield the crude product as yellow-brown solid (3.59 g; 85.5%). This was purified by recrystallization from a mixture of methylene chloride and methanol to afford the pure, titled benzofuran compound (V') as yellow-brown plates with m.p. 168°-169° C.

EXAMPLE 2

Synthesis of (1'S,2'S)-2-[carbo-(2-trimethylsilyl)ethoxymethyl]-3-[1',2'-dimethyl-ethylenedioxymethyl]-4,5-dihydroxyanthraquinone The titled compound (VII') was synthesized through the following route which corresponds to Stage B of the reaction scheme.

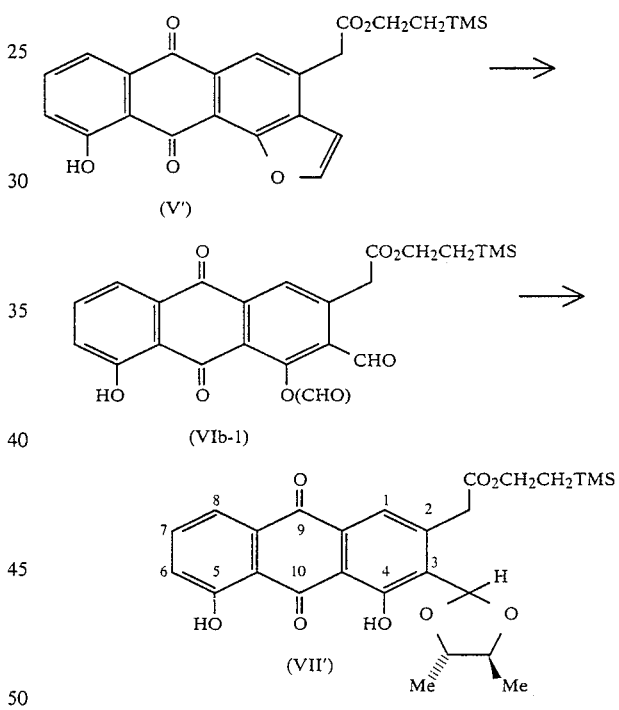

(a) Compound (V') (420 mg, 1 mmol) obtained in Example 1 above was dissolved in anhydrous methylene chloride (200 ml) and the solution was cooled to −78° C. Into the solution were introduced first ozone for 10 minute to effect ozonolysis (corresponding to the step (iv) of the third aspect process of this invention), and then nitrogen gas at −78° C. for 40 minutes and dimethyl sulfide (20 ml) was added to remove the excess ozone. The mixture was warmed to room temperature, the reaction solution was stirred at room temperature for further 1 hour and then concentrated in vacuo to yield the aldehyde compound (VIb-1) as yellow-brown crystals. This was used for the next step without purification.

(b) The crude aldehyde compound (VIb-1) thus obtained and L-(+)-2,3-butandiol (225 mg, 2.5 mmol; 0.5 molar equivalents) were added to dry toluene (40 ml), and the mixture was refluxed for 4 hours under nitrogen gas in the presence of a catalytic amount of pyridinium p-toluenesulfonate (75 mg, 0.3 mmol; 0.3 molar equivalents) to conduct the condensation reaction (corresponding to the step (v) of the third aspect process of this invention). The reaction solution was concentrated in vacuo and the resulting residue was purified by preparative silica gel thin layer chroamtography with elution with benzene-ethyl acetate (10:1) to yield the titled compound (VII') (423 mg; 85% from compound V') as yellow crystals. This was purified by recrystallization from methanol to yield pure acetal compound (VII') as yellow needles, m.p. 118°–119° C.

EXAMPLE 3

Synthesis of (1'R,1"S,2"S)-2-[carbo(2-trimethylsilyl)ethoxy]methyl-3-[1'-(2"-hydroxy-1"-methyl)-propyloxy-3'-oxo]pentyl-4,5-dihydroxyanthraquinone The titled compound (IIa) was synthesized by the following step which corresponds to Stage C-1 of the reaction scheme.

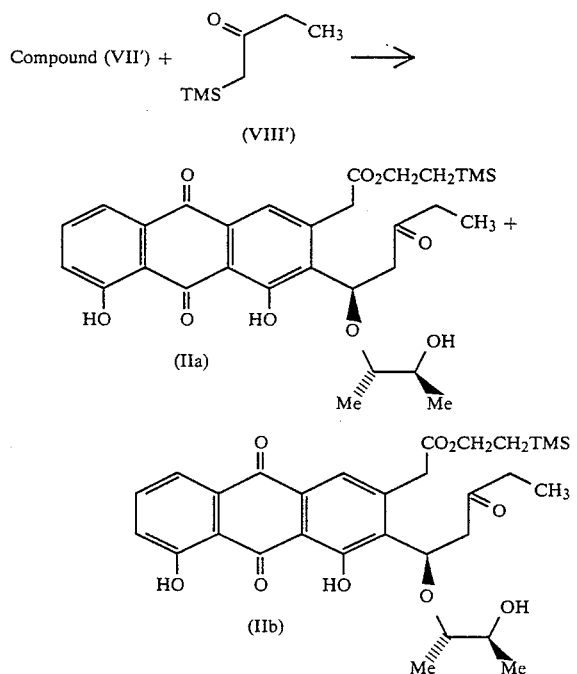

Compound (VII') (49.8 mg, 0.1 mmol) obtained in Example 2 above and ethyl-(trimethylsilyl)methylketone (VIII) [i.e. 1-(trimethylsilyl)-2-butanone] (288 mg, 2 mmol; 20 molar equivalents) were dissolved in anhydrous acetonitrile (15 ml), and to the solution was added at −20° C. a solution of stannic chloride (SnCl₄) (108 mg, 0.3 mmol, 3 molar equivalents, freshly distilled) in anhydrous methylene chloride (0.5 ml) dropwise over 15 minutes. The reaction mixture was further stirred at a temperature of −20° C.–−13° C. for 1.5 hours to conduct the aldol condensation (corresponding to a first alternative procedure of the step (vi) of the third aspect process of this invention). Then, saturated aqueous sodium carbonate (3.5 ml) was added to the reaction mixture at −20° C. The reaction mixture was warmed to room temperature and was extracted with methylene chloride. The combined organic extract was dried over anhydrous sodium sulfate and concentrated in vacuo. The oily residue was purified by preparative silica gel thin layer chromatography with elution with chloroform-ethyl acetate (20:1) to yield compound (IIa) (49.6 mg; 87%) and compound (IIb) (2.81 mg; 5.0%).

Compound (IIa) was purified by recrystallization from hexane as yellow fine plates, m.p. 81°–83° C.

EXAMPLE 4

Synthesis of (8S, trans)-8-ethyl-10-[2'(S)-hydroxy-1'(S)-methylpropyloxy]-7,8,9,10-tetrahydro-1,8,11-trihydroxy-5,12-naphthacenedione (a) Keto-ester compound (1) (40.05 mg, 0.07 mmol) which has the formula:

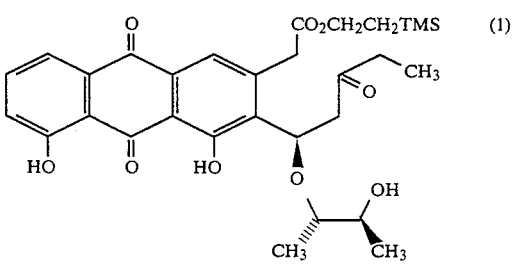

wherein TMS is trimethylsilyl group (which was prepared in Example 3 and mentioned as compound IIa) was dissolved in anhydrous tetrahydrofuran (12 ml), and to the solution was added 1,5-diazabicyclo[4,3,0]nonene-5 (DNB) (26.8 mg, 0.211 mmol; 5 molar equivalents) in one portion at room temperature under nitrogen gas. The mixture was stirred for 6 hours to conduct the cyclization reaction (corresponding to Stage D of the flow sheet and also to the step (vii) of the third aspect process of this invention), after which 1N hydrochloric acid (0.35 ml) and ethylether (70 ml) were added successively. The ether extract was washed with saturated aqueous sodium chloride, dried over anhydrous sodium sulfate and concentrated in vacuo to yield an oily residue. The residue was purified by preparative this layer chromatography on silica gel with elution with benzene-ethyl acetate (5:2 by volume) to afford compound (2) (29.28 mg; 73%) together with compound (3) (4.76 mg; 11.9%) with m.p. 187°–189° C.

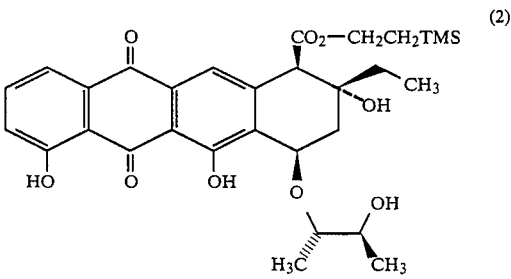

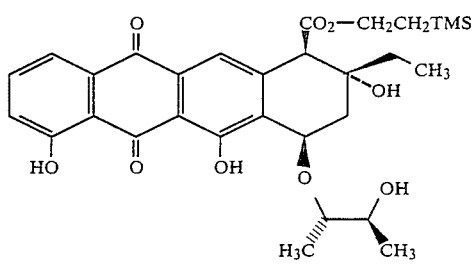

(3)

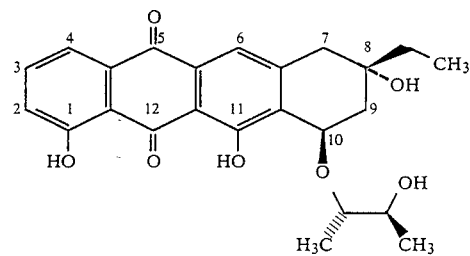

(4)

Compound (2) was purified by recrystallization from methanol, as orange plates, m.p. 117°–118° C.; $[\alpha]_D$—230° (c 0.053, chloroform-methanol (1:1)).

(b) To a solution of compound (2) (28.05 mg, 0.05 mmol) in anhydrous tetrahydrofuran (3 ml) was added dropwise 1M solution of tetra-n-butylammonium fluoride in tetrahydrofuran (400 μl, 0.4 mmol) at room temperature under nitrogen gas, and the mixture was stirred for 6 hours to effect the decarboxylation reaction (corresponding to Stage E of the flow sheet and also to the step (viii) of the third aspect process of this invention). The reaction solution, after the addition of 1N hydrochloric acid (400 μl), was diluted with methylene chloride and dried by passage through a short cotton column. The dried solution was concentrated in vacuo and the residue was purified by preparation silica gel-thin layer chromatography with elution with benzene-ethyl acetate (5:2) to afford the titled compound (4) (15.69 mg; 75%).

Compound (4) was purified by recrystallization from hexane-benzene to give yellow crystals with m.p. 139°–141° C. and $[\alpha]_D$—113° (c 0.053, chloroform-methanol (1:1)).

Compound (4) was also obtained from the minor compound (3) in comparable yield. For preparative purposes, it was possible to carry out the transformation of compound (1) to compound (4) without isolation and separation of the compounds (2) and (3) in about 65–70% overall yield.

EXAMPLE 5

Synthesis of (1′R,1″S,2″S)-2-[carbo(2-trimethylsilyl)ethoxymethyl]-3-[1′-(2″-hydroxy-1″-methyl)propyl-3′,4′-dioxopentyl]-4,5-dihydroanthraquinone The titled compound of formula (IIf) was synthesized through the following route which corresponds to Stage C-2 of the reaction scheme.

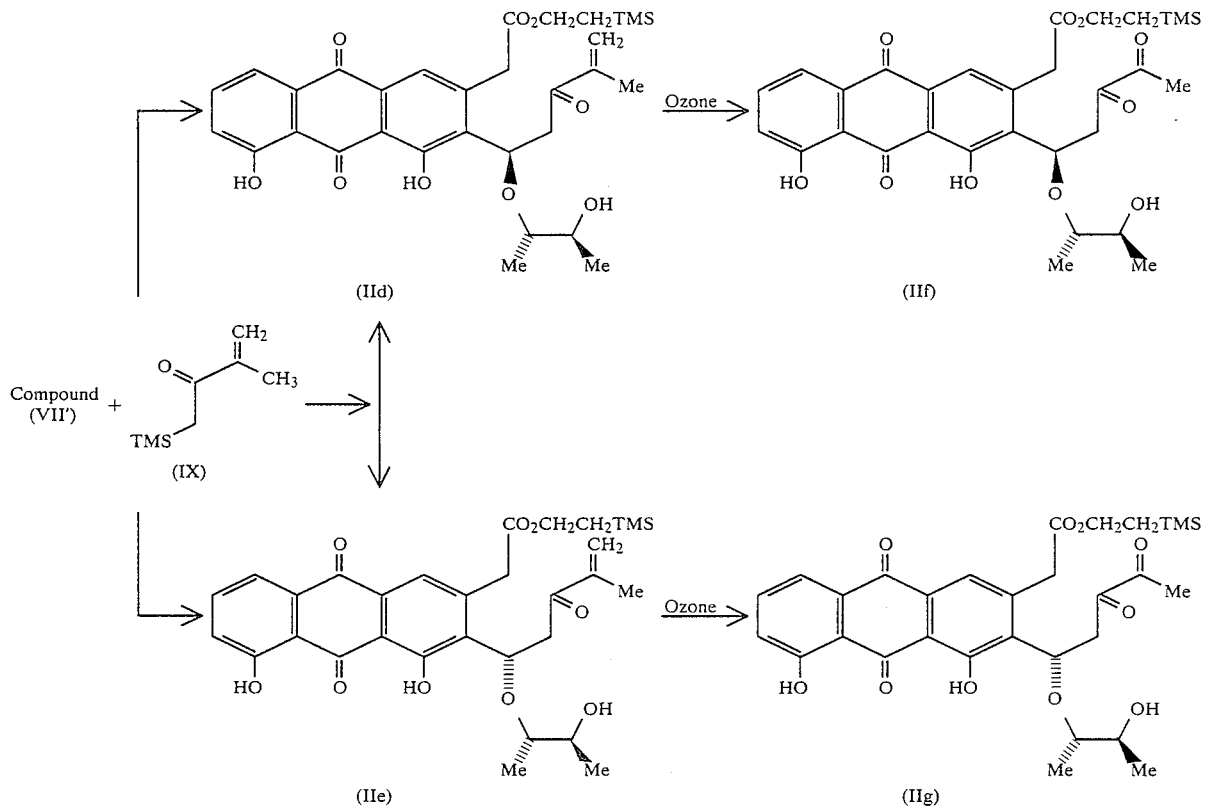

(a) Acetal compound (VII′) (99.6 mg, 0.2 mmol) obtained in Example 2 above and 2-propenyl-(trimethylsilyl)-methylketone (IX) [namely, 3-methyl-1-(trimethylsilyl)-3-buten-2-on] (368 μl, 4 mmol; 20 molar equivalents) were dissolved in dry toluene (40 ml), and the solution was cooled to −78° C., followed by dropwise addition of saturated solution of boron trifluoride in dry toluene (32 ml) (prepared at −78° C.) over 2 hours, during which there occurred the aldol condensation reaction (corresponding to a second alterative procedure of the step (vi) of the third aspect process of this invention). To the resulting deep red solution was added saturated aqueous sodium hydrogen carbonate (14 ml) at −78° C. and the reaction mixture was warmed to room temperature. The reaction mixture was extracted with methylene chloride, and the extract was dried over anhydrous sodium sulfate and concentrated in vacuo. The brown oily residue was purified by preparative silica gel thin layer chromatography with elution with benzene-ethyl acetate (10:1) to give a yellow oily mixture of compound (IId) and compound (IIe) (95.92 mg; 82.4%).

The oily mixture (95.92 mg; 0.165 mmol) was dissolved in methanol (96 ml) and the solution was cooled to −78° C., and ozone was introduced into the solution at −78° C. over 5 minutes (corresponding to the oxidation step in the second alternative procedure of the step (vi) of the third aspect process of this invention), and then nitrogen gas was bubbled thereinto at −78° C. over 40 minutes to remove the excess ozone. Then, dimethyl sulfide (1.65 ml) was added to the reaction mixture at −78° C. and the reaction mixture was warmed to room temperature and stirred for further 1 hour. The solvent was distilled off in vacuo to leave a brown oily residue. This was purified by preparative silica gel thin layer chromatography with elution with benzene-ethyl acetate (10:1) to yield the tilted compound (IIf) (72.35 mg; 75.2%) and compound (IIg) (5.71 mg; 6%) as yellow oil.

EXAMPLE 6

Synthesis of (8S-trans)-8-acetyl-10-[2'(S)-hydroxy-1"(S)-methylpropyloxy]-7,8,9,10-tetrahydro-1,8,11-trihydroxy-5,12-naphthacenedione (a) α-Diketone compound (5) (72.4 mg, 0.12 mmol) of the formula:

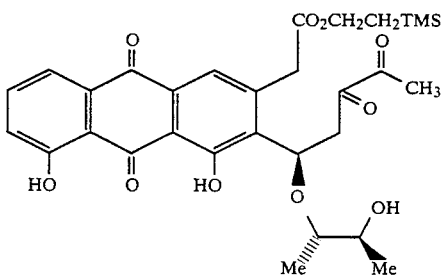

wherein TMS is trimethylsilyl and Me is methyl (which was prepared in Example 5 and mentioned as compound IIf) was dissolved in anhydrous tetrahydrofuran (12.4 ml), and DBN (76.9 mg, 0.62 mmol; 5 molar equivalents) was added in one portion to the solution at room temperature. The resulting violet solution was stirred for 10 minutes to effect the cyclization reaction (the step (vii) of the third aspect process of this invention), after which 1N hydrochloric acid (0.62 ml) was added and the reaction mixture was diluted with methylene chloride. The reaction mixture was dried by passing through a cotton column. After the solvent was distilled off, the residual yellow solid was purified by preparative silica gel thin layer chromatography with elution with chloroform-ethyl acetate (20:1) to yield yellow solid compound (6) (44.2 mg; 61%) and compound (7) (17.4 mg; 24%) of the formulae:

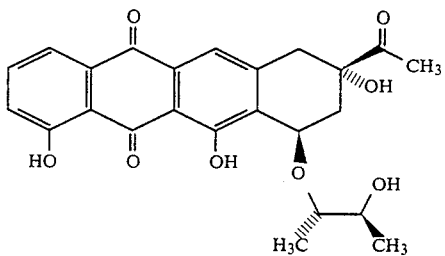

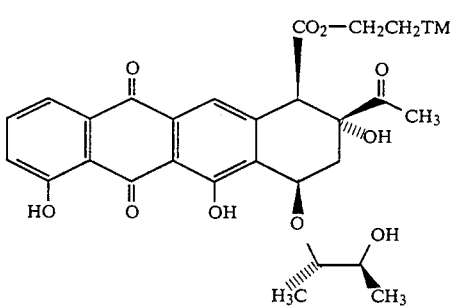

Compound (6) was recrystallized from a mixture of benzene and hexane to give yellow plates, m.p. 108°–109° C. and $[\alpha]_D-26°$ (c 0.10, chloroform-methanol (1:1)).

Compound (7) was recrystallized similarly from a mixture of benzene and hexane to give yellow-orange powder, m.p. 167°–170° C.

(b) Cyclic ketone compound (6) prepared in step (a) (71.4 mg, 0.122 mmol) was dissolved in dry N,N-dimethylformamide (8 ml), and to the solution was added a 1M solution of tetra-n-butyl ammonium fluoride (n-Bu$_4$NF) in tetrahydrofuran (0.98 ml, 0.98 mmol; 8 molar equivalents) dropwise over 5 minutes at room temperature. The violet-colored mixture was stirred for 6 hours to effect the decarboxylation reaction (the step (viii) of the third step process of this invention), after which 1N hydrochloric acid (0.98 ml) was added and the reaction mixture was diluted with methylene chloride. The reaction was dried by passing through a cotton column. The dried solution was concentrated in vacuo and the residual yellow solid was purified by preparative silica gel thin layer chromatography eluting with benzene-ethyl acetate (1:1) to afford compound (8) (42.6 mg; 78.8%) as yellow crystals.

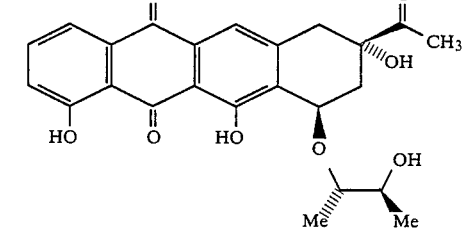

Compound (8) was recrystallized from a mixture of benzene and hexane to give the pure 11-deoxy compound as yellow powder with m.p. 138°–140° C. and [α]$_D$ −49° (c 0.10, chloroform-methanol (1:1)).

Compound (8) was also prepared from compound (7) [a stereoisomer of compound (6)] in the same manner as above in a yield of 61%. Compound (8) was obtained from compound (5) in overall yield of 65% without isolation and separation of the intermediate compounds.

EXAMPLE 7

(a) Synthesis of 4-[carbo(2'-trimethylsilyl)ethoxymethyl]-8-methoxyanthraquinofuran (VI')

Compound (VI') was synthesized by the following step which corresponds to Stage A-1 of the reaction scheme.

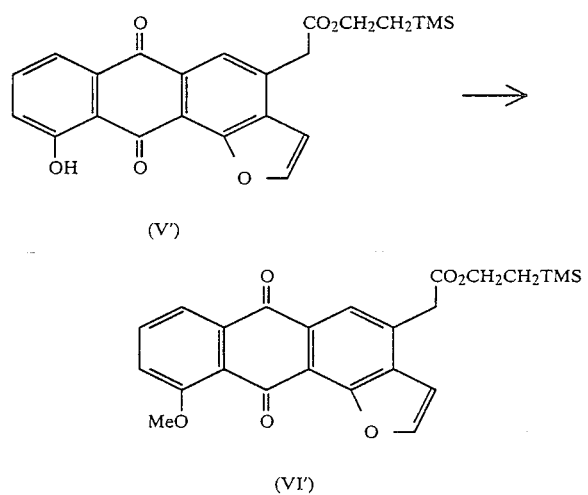

The benzofuran compound (V') (1.05 g, 2.5 mmol) obtained in Example 1 above, silver oxide (Ag$_2$O) (8.69 g, 37.5 mmol; 15 molar equivalents) and methyl iodide (35.5 g, 0.25 mol; 100 molar equivalents) were admixed with chloroform (250 ml), and the mixture was heated to 50° C. under nitrogen gas with stirring for 64 hours to conduct the methylation reaction (corresponding to optional alkylation step (iii) of the third aspect process of this invention).

The reaction solution was passed through a Celite bed to remove the precipitated inorganic materials. The Celite bed and the inorganic precipitate were washed with methylene chloride. The reaction solution having passed through the Celite bed was combined with the methylene chloride washings, and the combined solution was concentrated in vacuo. The residue was purified by preparative thin layer chromatography with elution with benzene-ethyl acetate (5:2) to yield the titled compound (VI') (990 mg; 91.3%) as yellow solid. This was purified by recrystallization from methanol to yield compound (VI') as yellow powder, m.p. 124°–124.5° C.

(b) Synthesis of (1'S,2'S)-2-[carbo-(trimethylsilyl)ethoxymethyl]-3-[1',2'-dimethylethylenedioxymethyl]-4-hydroxy-5-methoxyanthraquinone (VII')

Compound (VI') ⟶

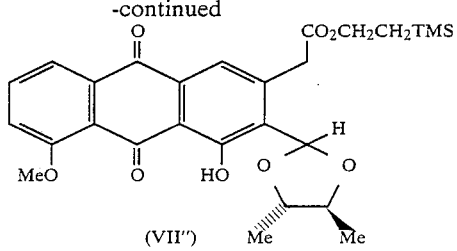

Compound (VI') obtained in step (a) above was treated in the same manner as in Example 2 to yield the titled compound (VII'').

(c) Synthesis of (1'R,1''S,2''S)-2-[carbo(2-trimethylsilyl)ethoxymethyl]-3-[1'-(2''-hydroxy-1''-methyl)-propyloxy-3'-oxopentyl]-4-hydroxy-5-methoxyanthraquinone (IIh)

Compound (VII'') ⟶

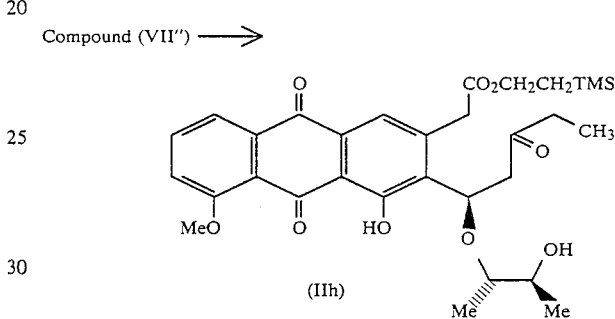

Compound (VII'') obtained in step (b) above was treated in the same manner as in Example 3 to yield the titled compound (IIh).

EXAMPLE 8

Synthesis of (8S,trans)-8-ethyl-10-[2'(S)-hydroxy-1'(S)-methylpropyloxy]-7,8,9,10-tetrahydro-8,11-dihydroxy-1-methoxy-5,12-naphthacenedione

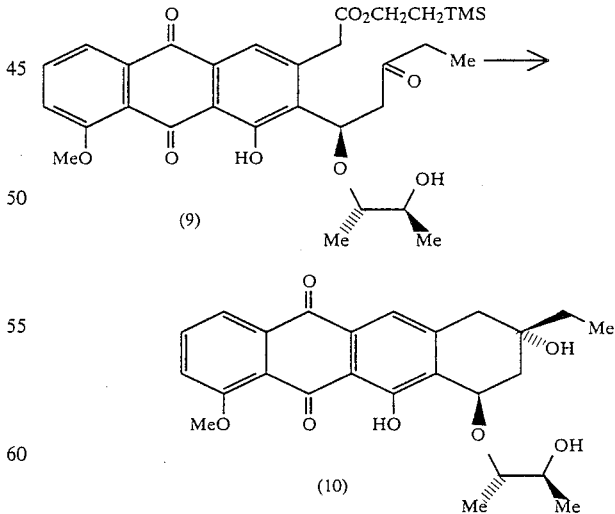

Keto-ester compound (9) (which was prepared in Example 7 and mentioned as compound IIh) was treated in the same manner as in Example 4 (a) and (b) to yield the titled compound (10) in a yield comparable to that in Example 4.

pmr (80 MHz): δ1.0–2.0 (m, 8-CH₂, CH₃ and 1'-CH₃, 2'-CH₃), 4.27 (s, 3H, OCH₃), 5.48 (t, 1H, 10-H); 7.5–8.1 (m, 4H, 2-H, 3-H, 4-H and 6-H).

EXAMPLE 9

Synthesis of (1'R,1"S,2"S)-2-[carbo(2-trimethylsilyl)ethoxymethyl]-3-[1'-(2"-hydroxy-1"-methyl)-propyloxy-3',4'-dioxopentyl]-4-hydroxy-5-methoxyanthraquinone (IIi)

Compound (VII") ⟶

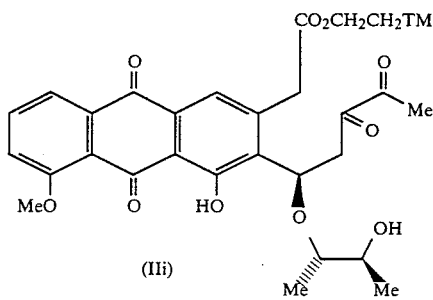

(IIi)

Compound (VII') obtained in step (b) of Example 7 was treated in the same manner as in Example 5 to yield the titled compound (IIi).

EXAMPLE 10

Synthesis of (8S,trans)-8-acetyl-10-[2'(S)-hydroxy-1'(S)-methylpropyloxy]-7,8,9,10-tetrahydro-8,11-dihydroxy-5,12-naphthacenedione

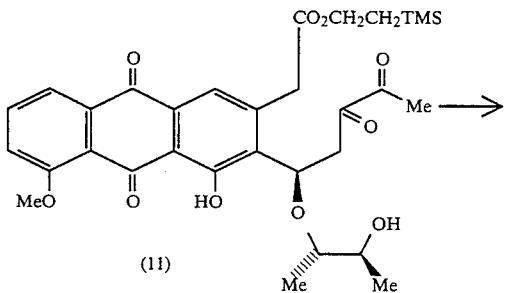

(11)

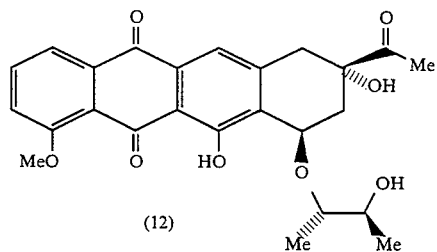

(12)

Keto-ester compound (11) (which was prepared in Example 9 and mentioned as compound IIi) was treated in the same manner as in Example 6 (a) and (b) to afford the titled compound (12) in a yield comparable to that in Example 6.

pmr (80 MHz): δ0.75–1.25 (m, 1'-CH₃ and 2'-CH₃), 2.35 (s, 3H, 14-CH₃), 4.17 (s, 3H, OCH₃), 5.40 (t, 1H, 10-H), 7.3–7.8 (m, 4H, 2-H, 3-H, 4-H and 6-H).

EXAMPLE 11

Synthesis of 4-[2'-(trimethylsilyl)ethoxycarbonylmethyl]anthraquinofuran (V")

Compound (V") was synthesized through the following route which corresponds to Stage A of the reaction scheme.

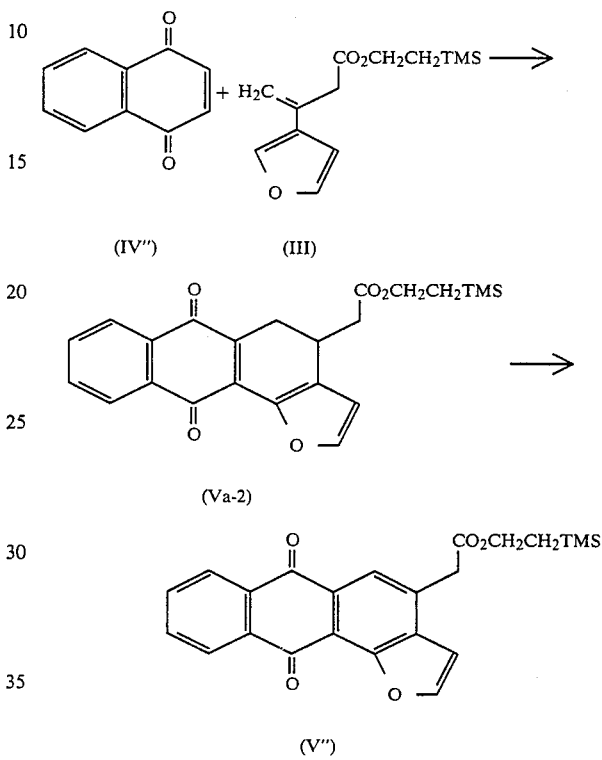

(a) Naphthoquinone of formula (IV") (316 mg, 2.02 mmol) and a furandiene compound of formula (III) (0.83 g, 50 mmol) were dissolved in toluene (10 ml), and the solution was cooled to −20° C., followed by addition of tris(D-bromophenyl)ammoniumyl hexachloroantimonate[(p-BrC₆H₄)₃NSbCl₆] (82 mg, 0.01 mmol) in one portion with stirring under nitrogen. The mixture was stirred at −20° C. for 10 minutes and then warmed to 0° C. After stirring for 15 minutes, an additional amount (0.16 g, 10 mmol) of the furandiene compound (III) was added to the mixture at 0° C. and the stirring was continued for further 15 minutes at 0° C. and then at room temperature for further 15 minutes to complete the desired Diels-Alder reaction (corresponding to the step (i) of the third aspect process of this invention). The reaction mixture was filtered through a pad of Celite and the Celite pad was washed with ether. The filtrate was combined with the ether washings, and the combined solution was concentrated in vacuo to afford a crude product. This was purified by silica gel column chromatography with elution with 5% ethyl acetate-benzene, affording compound (Va-2) as an orange solid (497 mg; 76%).

(b) The adduct compound (Va-2) (497 mg, 1.53 mmol) was dissolved in chloroform (50 ml) and diisopropylethylamine (0.50 ml, 2.9 mmol) was added to the solution. The reaction mixture was stirred under air atmosphere at room temperature for 16 hours for oxidation (corresponding to the step (ii) of the third aspect process of this invention) and concentrated in vacuo. The crude product recovered as residue was purified by silica gel column chromatography with elution with 10% ethyl acetate-benzene, affording 425 mg of compound (V″) (425 mg; 86%).

EXAMPLE 12

Synthesis of (1′S,2′S)-2-[carbo(2-trimethylsilyl)ethoxymethyl]-3-[1′,2′-dimethylethylenedioxymethyl]-4-hydroxyanthraquinone (VII‴)

Compound (VII‴) was synthesized by the following step which corresponds to Stage B of the reaction scheme.

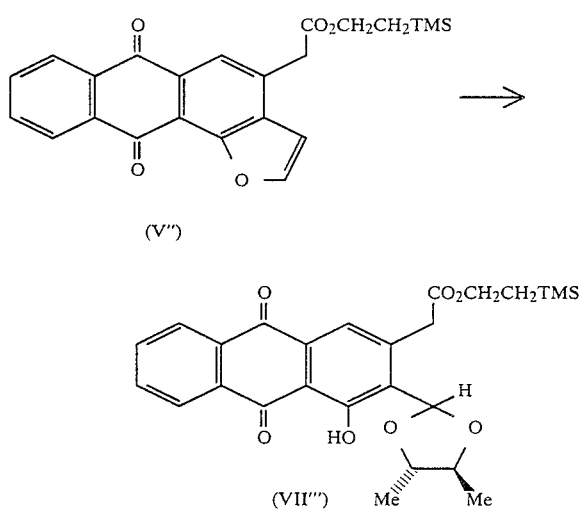

Compound (V″) obtained in step (b) of Example 11 was treated in the same manner as in Example 2 to yield the titled compound (VII‴).

EXAMPLE 13

Synthesis of (1′R,1″S,2″S)-2-[carbo(2-trimethylsilyl)ethoxymethyl]-3-[1′-(2″-hydroxy-1″-methyl)-propyloxy-3′-oxopentyl]-4-hydroxyanthraquinone (IIj)

Compound (IIj) was synthesized by the following step which corresponds to Stage C-1 of the reaction scheme.

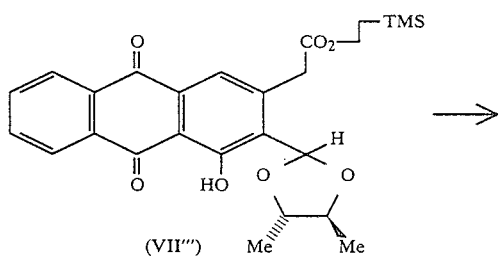

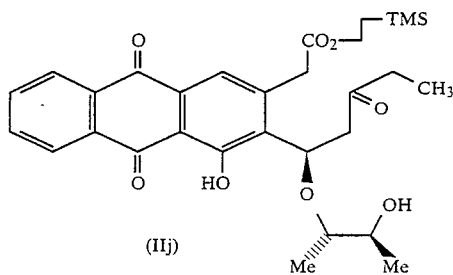

Compound (VII‴) obtained in Example 12 above was treated in the same manner as in Example 3 to yield the titled compound (IIj).

EXAMPLE 14

Synthesis of (8S,trans)-8-ethyl-10-[(2′(S)-hydroxy-1′(S)-methyl)-propyloxy]-7,8,9,10-tetrahydro-8,11-dihydroxy-5,12-naphthacenedione

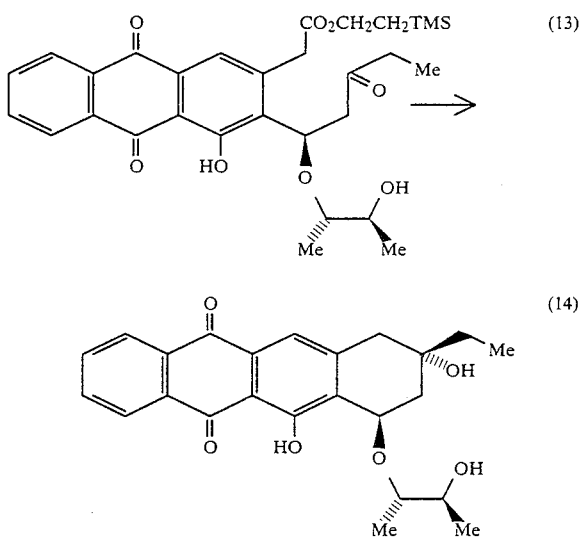

Keto-ester compound (13) (which was prepared in Example 13 and mentioned as compound IIj) was treated in the same manner as in Example 4 (a) and (b) to yield the titled compound (14) in a yield comparable to that in Example 4.

pmr (80 MHz): δ, 1.04–1.23 (m, 6H, 8—CH$_2$CH$_3$ and 1′-CH$_3$, 2′-CH$_3$), 3.46 (t, 1H, 10-H), 7.54 (s, 1H, 6-H), 7.6–8.3 (m, 4H, 1-H, 2-H, 3-H and 4-H).

EXAMPLE 15

Synthesis of (1′R,1″S,2″S)-2-[carbo(2-trimethylsilyl)ethoxymethyl]-3-[1′-(2″-hydroxy-1″-methyl)-propyloxy-3′,4′-dioxopentyl]-4-hydroxyanthraquinone (IIk)

Compound (VII‴) ⟶

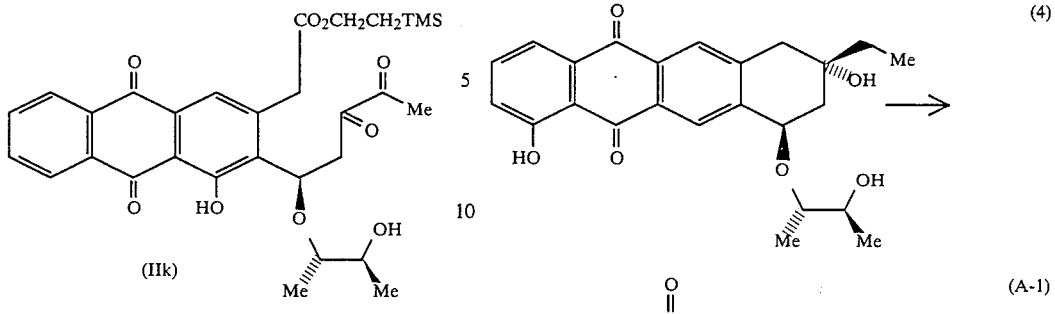

Acetal compound (VII''') obtained in Example 12 was treated in the same manner as in Example 5 to afford the titled compound (IIk).

EXAMPLE 16

Synthesis of (8S,trans)-8-acetyl-10-[2'(S)-hydroxy-1'(S)-methylpropyloxy]-7,8,9,10-tetrahydro-8,11-dihydroxy-5,12-naphthacenedione

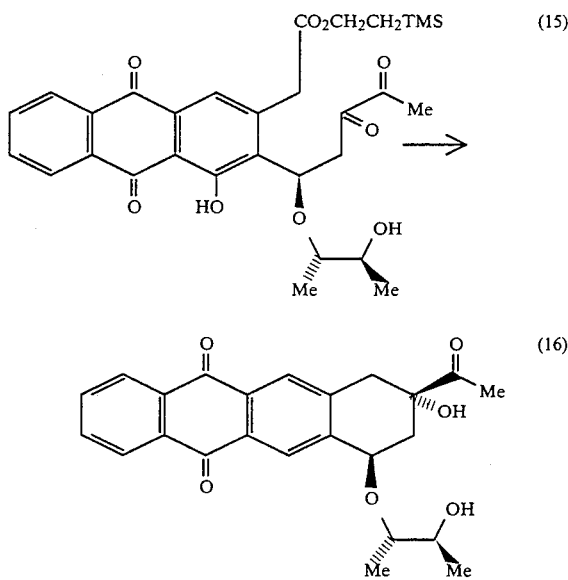

Keto-ester compound (15) (which was prepared in Example 15 and mentioned as compound IIk) was treated in the same manner as in Example 6 (a) and (b) to yield compound (16) in a yield similar to that in Example 6.

pmr (80 MHz): δ, 1.10 and 1.20 (both d, 3H, 1'-CH₃ and 2'-CH₃), 2.38 (s, 3H, 14-CH₃), 3.46 (t, 1H, 10-H), 7.65 (s, 1H, 6-H), 7.7-8.3 (m, 4H, 1-H, 2-H, 3-H and 4-H).

The following Examples 17–22 illustrates that the compounds obtained by the process of this invention may be converted into daunomycinone derivatives.

EXAMPLE 17

Synthesis of 4-demethyl-11-deoxy-13-deoxodaunomycinone (A-1)

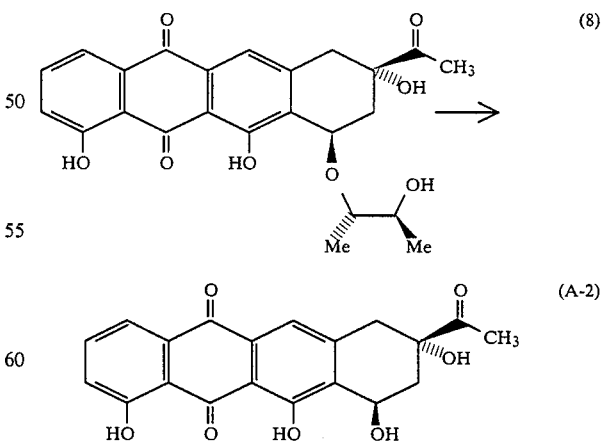

To compound (4) (38.4 mg, 0.090 mmol) obtained in step (b) of Example 4 was added trifluoroacetic acid (3 ml) dropwise over 2 minutes with cooling to −78° C. under argon gas. The cooling bath was warmed to 10° C. over 3 hours and the mixture was stirred for further 1.7 hours and then concentrated in vacuo. The residue was dissolved in acetone (7 ml) and a 5% aqueous sodium hydrogen carbonate (3 ml) (freshly prepared) was added thereto. The mixture was stirred for 1 hour, diluted with water (16 ml) and then extracted with dichloromethane three times. The organic layers so separated were combined, dried over anhydrous sodium sulfate and concentrated in vacuo to leave a crude product.

The crude product was purified by preparative thin layer chromatography with twice elution with 12% ethyl acetate-benzene to afford the desired product in a pure state (27.0 mg; 8.5%). This was further purified by recrystallization from hot benzene to yield compound (A-1) as red crystals with m.p. 189°–191° C. and [α]_D +148° (c 0.10, chloroform-methanol (1:1)).

EXAMPLE 18

Synthesis of 4-demethyl-11-deoxy-daunomycinone (A-2)

Compound (8) obtained in step (b) of Example 6 was treated with trifluoroacetic acid in the same manner as in Example 17 above to afford the titled compound (A-2) in a yield comparable to that obtained in Example 13. m.p. 173°–176° C.; $[\alpha]_D+195°$ (c 0.10, chloroform-methanol (1:1)).

EXAMPLE 19

Synthesis of 11-deoxy-13-deoxo-daunomycinone (A-3)

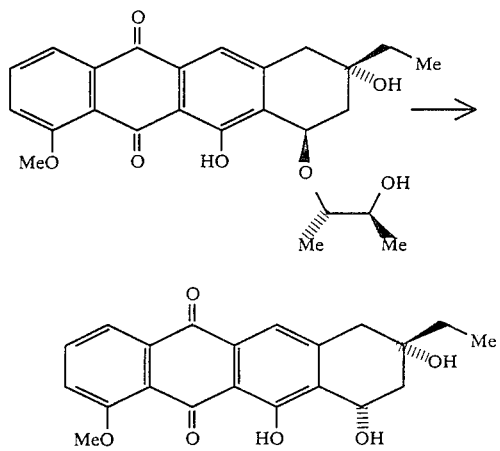

Compound (10) obtained in Example 8 above was treated with trifluoroacetic acid at −78° C. in the same manner as in Example 17 to afford the titled compound (A-3) in a yield comparable to that obtained in Example 17. m.p. 213°–216° C.; $[\alpha]_D+132°$ (c 0.10, chloroform-methanol (1:1)).

EXAMPLE 20

Synthesis of 11-deoxy-daunomycinone (A-4)

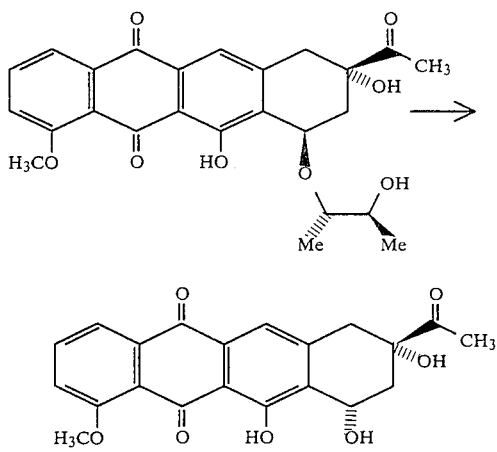

Compound (12) obtained in Example 10 was treated with trifluoroacetic acid in the same manner as in Example 17 to afford the titled compound (A-4) in a yield comparable to that obtained in Example 17. m.p. 215°–219° C.; $[\alpha]_D+174°$ (c 0.10, chloroform-methanol (1:1)).

EXAMPLE 21

Synthesis of 4-demethoxy-11-deoxy-13-deoxo-daunomycinone (A-5)

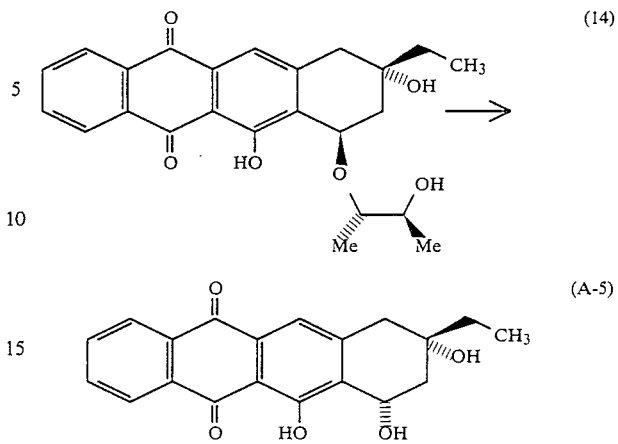

Compound (14) obtained in Example 14 was treated with trifluoroacetic acid at −78° C. in the same manner as in Example 17 to afford the titled compound (A-5) in a yield comparable to that obtained in Example 17. m.p. 186°–188° C.; $[\alpha]_D+81°$ (c 0.10, chloroform-methanol (1:1)).

EXAMPLE 22

Synthesis of 4-demethoxy-11-deoxy-daunomycinone (A-6)

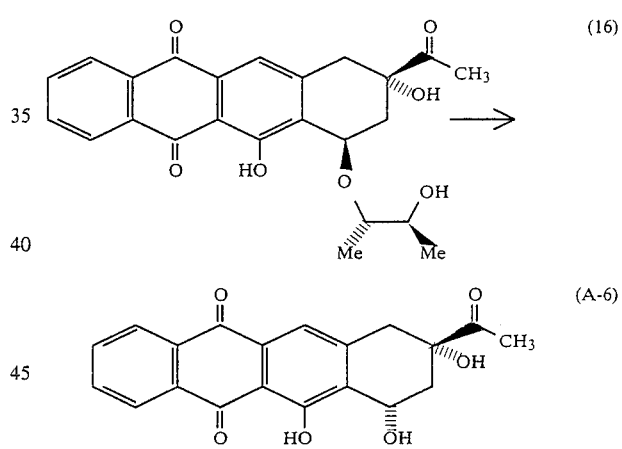

Compound (16) obtained in Example 16 was treated in the same manner as in Example 17 to yield the titled compound (A-6) in a yield comparable to that obtained in Example 17. m.p. 201°–213° C.; $[\alpha]_D+124°$ (c 0.10, chloroform-methanol (1:1)).

The following Examples 23–24 illustrate the preparation of the starting materials for use in the process of this invention.

EXAMPLE 23

Synthesis of furan diene of the formula

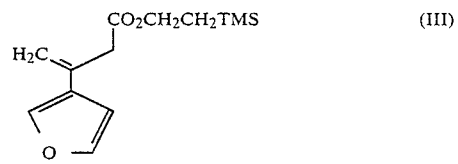

(a) Preparation of furyl methyl ketone

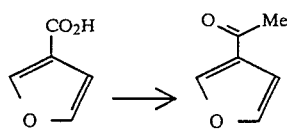

3-Furoic acid (25.0 g, 0.233 mmol) was dissolved in dry ether (1.1 l), and to the solution was added a solution of 1.42M methyllithium (0.51 mol) in ether (370 ml) dropwise over 55 minutes at 0° C., with stirring under nitrogen. The reaction mixture was stirred at room temperature for 10 hours and then poured into ice-cold 1N hydrochloric acid (1 l) under good stirring. The ether layer was separated and the water layer was extracted with ether. The combined ether layers were washed first with 1N sodium hydroxide (134 ml) and then with saturated aqueous sodium chloride (200 ml×2), dried over anhydrous sodium sulfate and concentrated in vacuo at ca. 5° C. and then briefly at room temperature.

The crude product (23.25 g; 92%) thus obtained was used for the next step without purification.

A pure sample was obtained by sublimation (40° C. at 20 mmHg) as colorless needles, m.p. 51°-51.5° C.

(b) Preparation of β-(trimethylsilyl)ethyl ester of bromoacetic acid

β-Trimethylsilylethanol (49.5 g, 0.42 mol) and N,N-dimethylaniline (53.3 g, 0.44 mol) were dissolved in anhydrous methylene chloride (250 ml), and to the ice-cold solution was added dropwise bromoacetyl bromide (89 g, 0.44 mol) over 30 minutes, at 0° C. with stirring under nitrogen gas. The reaction solution was stirred at room temperature for 1 hour, diluted with methylene chloride (300 ml), washed successively with 1N hydrochloric acid (100 ml×5), saturated aqueous sodium hydrogen carbonate (100 ml×3) and saturated aqueous sodium chloride (100 ml) once and dried over anhydrous sodium sulfate.

The dried mixture was evaporated in vacuo to remove the solvent and the residue was distilled in vacuo to give the desired compound (95.67 g; 95.3%) as colorless oil with b.p. 82°-84° C. at 3 mmHg.

(c) Preparation of phosphonate compound of formula (a)

TMS-CH$_2$-CH$_2$O-CO-CH$_2$Br→TMS-CH$_2$CH$_2$-O-CO-CH$_2$-P(O)(OEt)$_2$     (a)

To triethyl phosphite (34.7 g, 0.209 mol) was added dropwise over 1 hour at 70° C. the bromoacetic acid ester (50 g, 0.209 mol) obtained in the above step (b). Then, the reaction mixture was slowly heated to 170° C., and the resulting ethyl bromide was removed by distillation. After heating at that temperature for 16 hours, the reaction solution was distilled in vacuo to afford compound (a) (59.1 g; 95.4%) as colorless oil with b.p. 141°-145° C. at 2 mmHg.

(d) Preparation of compound (b)

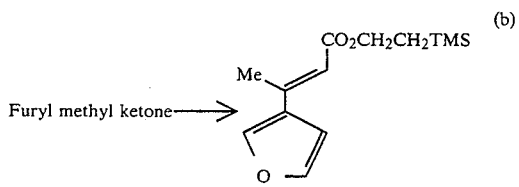

Sodium hydride (6.14 g, 0.154 mol) (newly washed with anhydrous hexane) was suspended in anhydrous tetrahydrofuran, and to the suspension was added dropwise the phosphonate compound of formula (a) (47.40 g, 0.16 mol) obtained in the above step (c) at room temperature over 30 minutes. A clear solution was formed, and after 40 minutes, the crude furyl methyl ketone (14.68 g, 0.134 mol) obtained in the above step (a) in the form of a solution in anhydrous tetrahydrofuran (200 ml) was added dropwise to said clear solution over 25 minutes at room temperature. The reaction mixture was further stirred at room temperature for 1 hour and then heated to 50° C. for 2 hours. After cooling to room temperature, water (830 ml) was added dropwise to the cooled reaction mixture and the aqueous layer formed was extracted with ether. The combined ether extracts were washed with water and then with saturated aqueous sodium chloride, dried over anhydrous sodium sulfate. The dried solution was concentrated in vacuo to leave a brown oil. This was purified by silica gel G-column chromatography using hexane-ethyl acetate (20:1) as eluent to afford compound (b) (24.58 g; 73%) as a colorless oil.

(e) Preparation of compound (c) which corresponds to compound (III')

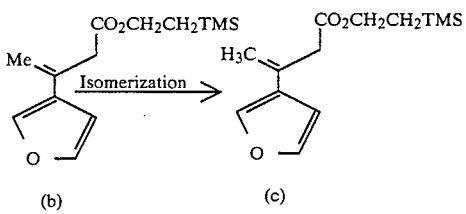

To a solution of anhydrous diisopropylamine (29.55 g, 0.293 mol) in anhydrous tetrahydrofuran (440 ml) was added a 2.35M solution of n-butyllithium (0.146 mol) in hexane (62.3 ml) dropwise over 1 hour, at 0° C. with stirring under nitrogen. The stirring was continued at that temperature for further 20 minutes. The reaction mixture was cooled to −78° C., to which was added a solution of compound (b) obtained in the above step (d) in the form of the conjugated ester (24.58 g, 0.0975 mol) in anhydrous tetrahydrofuran (50 ml) dropwise over 20 minutes. After the completion of the addition, the mixture was further stirred for 25 minutes. Then, phenol (15.5 g, 0.166 mol) was added in one portion to the reaction mixture at −78° C. under nitrogen gas and the mixture was stirred for 15 minutes, after which saturated aqueous ammonium chloride (540 ml) was added at a stroke and the reaction mixture was warmed to room temperature. Subsequently, water (150 ml) and ether (500 ml) were added to the reaction mixture. The organic layer was separated and the water layer was extracted with ether. The organic layer was combined with the ether extracts, washed with 1N aqueous sodium hydroxide (655 ml) and then with saturated aqueous sodium chloride, and dried over anhydrous sodium sulfate. The organic solution was concentrated in vacuo, and the residue was purified by passing through a short column of silica gel to yield a 3:1 mixture (23.65 g) of the de-conjugated ester of formula (c) and conjugated ester of formula (b). This mixture was used for the Diels-Alder reaction in step (a) of Example 1 given hereinbefore.

EXAMPLE 24

Synthesis of 2-propenyl-(trimethylsilyl)methyl ketone of formula (f) which was used in step (a) of Example 5

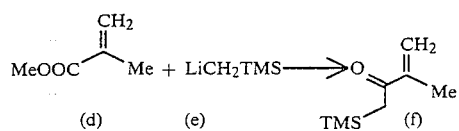

Lithium (750 mg, 107 mmol) and trimethylsilylmethyl chloride (6.6 ml, 47.28 mmol) were added to dry pentane and the mixture was heated to 100° C. for 4.5 hours under nitrogen gas. The resulting violet mixture containing compound (e) was cooled to 0° C., to which was added dropwise a solution of methyl methacrylate of formula (d) (2.5 ml, 23.64 mmol) in dry pentane (5 ml) over 15 minutes at 0° C. After stirring at 0° C. for 15 minutes, the mixture was further stirred at room temperature for 2 hours. The reaction mixture was then poured into ice water (15 ml), followed by extraction with ether. The ether extract was dried over anhydrous sodium sulfate and concentrated in vacuo to yield a crude product (3.73 g) as yellow oil. This crude product was purified by distillation in vacuo to afford the desired product of formula (f), i.e. the compound (IX) hereinbefore given, in the form of a colorless oil (1.9 g; 40%) with b.p. 72° C. at 1.5 mmHg.

What I claim is:

1. A compound of the formula

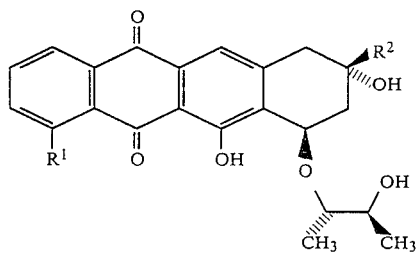

wherein $R^1$ denotes a hydrogen atom, a hydroxyl group or an alkoxyl group of 1–4 carbon atoms and $R^2$ denotes an ethyl group or an acetyl group.

2. A compound of claim 1 in which $R^1$ is a hydroxyl group and $R^2$ is an ethyl group.

3. A compound of claim 1 in which $R^1$ is a hydroxyl group and $R^2$ is an acetyl group.

4. A compound of claim 1 in which $R^1$ is a methoxy group and $R^2$ is an ethyl group.

5. A compound of claim 1 in which $R^1$ is a methoxy group and $R^2$ is an acetyl group.

6. A compound of claim 1 in which $R^1$ is a hydrogen atom and $R^2$ is an ethyl group.

7. A compound of claim 1 in which $R^1$ is a hydrogen atom and $R^2$ is an acetyl group.

8. A process for the production of a compound of the formula

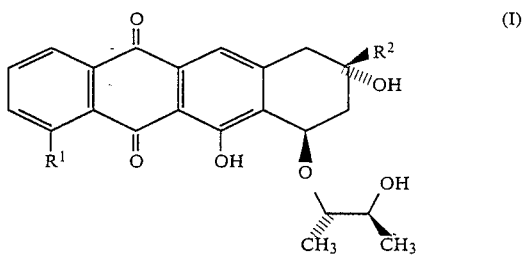

wherein $R^1$ denotes a hydrogen atom, a hydroxyl group or an alkoxyl group of 1–4 carbon atoms and $R^2$ denotes an ethyl group or an acetyl group, which comprises the steps of:

(a) cyclizing the compound of the formula

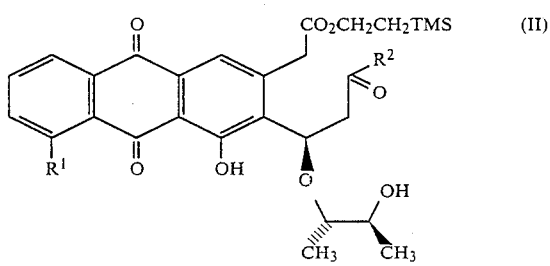

wherein $R^1$ and $R^2$ are as defined above and TMS denotes a trimethylsilyl group by treating with a base in an organic solvent to produce the compound of the formula

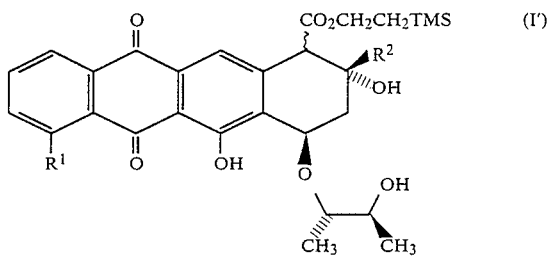

wherein $R^1$, $R^2$ and TMS are as defined above, and (b) decarboxylating the compound of the formula (I') by treating the latter with a tetra-alkyl ammonium fluoride or hydrogen fluoride in an organic solvent to produce the desired compound of the formula (I).

9. A process of claim 8 in which the compound of the formula (II) is cyclized by treating with 1,5-diazabicyclo[4.3.0]-nonene-5 in an anhydrous organic solvent.

10. A process of claim 8 in which the compound of the formula (I') is decarboxylated by reacting with tetra-n-butyl ammonium fluoride in an anhydrous organic solvent.

11. A process for the production of a compound of the formula (I)

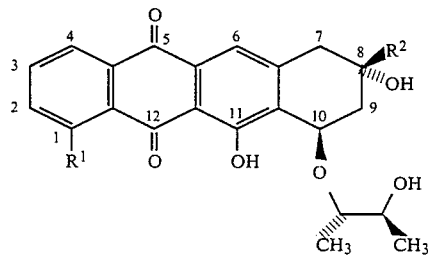 (I)

wherein $R^1$ and $R^2$ are as defined in claim 1, which comprises the consecutive steps of:

(i) subjecting a compound of the formula (III)

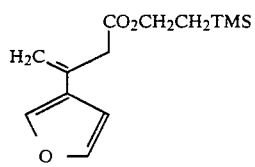 (III)

wherein TMS denotes a trimethylsilyl group, and a compound of the formula (IV)

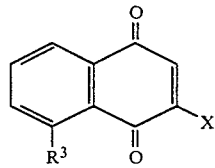 (IV)

wherein $R^3$ is a hydrogen atom or a hydroxyl group and X is a bromo group or a hydrogen atom, to Diels-Alder condensation, either under the thermal condition in the presence of 4,4'-thiobis(6-t-butyl-3-methylphenol) as a radical scavenger and an acid acceptor when the group X of the compound (IV) denotes a bromo group, or under the cation radical condition in the presence of a catalyst when the group X of the compound (IV) denotes a hydrogen atom, thereby to produce the compound of the formula (Va)

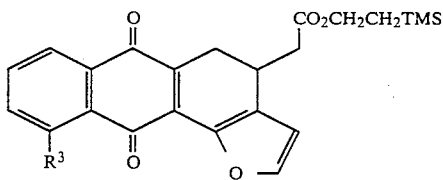 (Va)

wherein $R^3$ and TMS are as defined above, (ii) oxidizing the compound of the formula (Va) in the presence of a base to produce the compound of the formula (V)

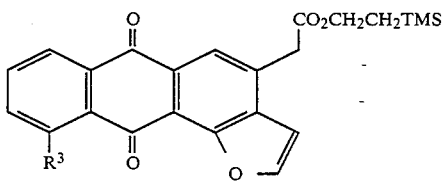 (V)

wherein $R^3$ and TMS are as defined above, (iii) optionally alkylating the group ($R^3$) of the compound of the formula (V) where $R^3$ denotes a hydroxyl group, by reacting with an alkyl iodide of 1–4 carbon atoms in an organic solvent, to produce the compound of the formula (VI)

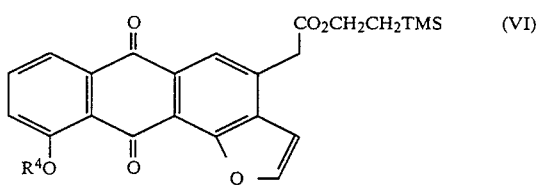 (VI)

wherein $R^4$ is an alkyl group of 1–4 carbon atoms and TMS is as defined above, (iv) ozonolyzing the compound of the formula (VIa)

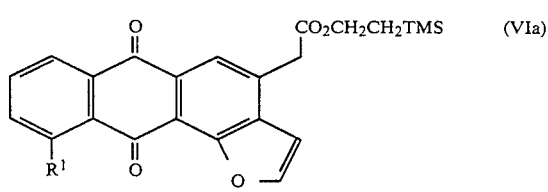 (VIa)

wherein $R^1$ is a hydrogen atom, a hydroxyl group or an alkoxyl group of 1–4 carbon atoms as defined above and TMS is as defined above [the compound of the formula (VIa) generically representing both the compound of the above formula (V) and the compound of the above formula (VI)], thereby to give the aldehyde compound of the formula (VIb)

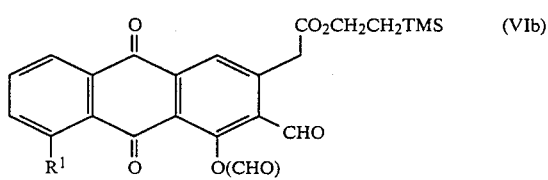 (VIb)

wherein $R^1$ and TMS are as defined above, (v) reacting the aldehyde compound of the formula (VIb) with L-(+)-2,3-butanediol in an inert organic solvent in the presence of an acid catalyst to produce an acetal compound of the formula (VII)

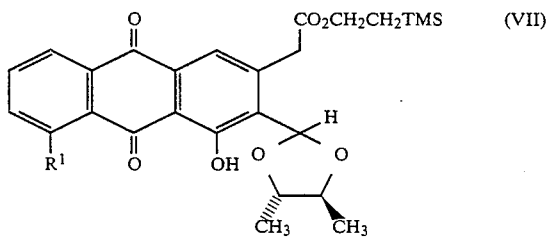 (VII)

wherein $R^1$ and TMS are as defined above, (vi) either condensing the acetal compound of the formula (VII) and 1-(trimethylsilyl)-2-butanone of the formula (VIII)

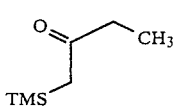

wherein TMS is a trimethylsilyl group to produce a compound of the formula (II')

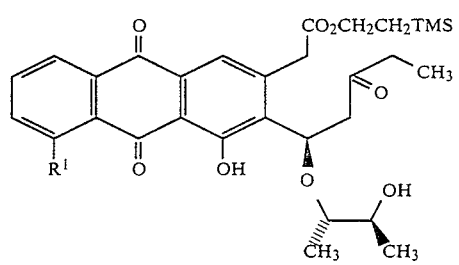

wherein R¹ and TMS are as defined above; or condensing the acetal compound of the formula (VII) and 3-methyl-1-(trimethylsilyl)-3-buten-2-on of the formula (IX)

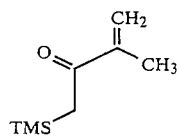

wherein TMS is as defined above to produce a compound of the formula (II'')

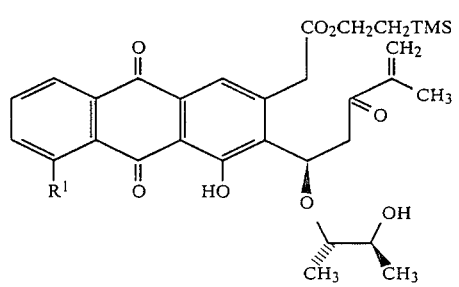

wherein R¹ and TMS are as defined above, followed by ozonolyzing the compound of the formula (II'') to produce a compound of the formula (II''')

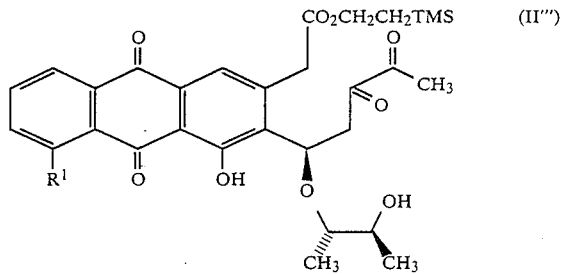

wherein R¹ and TMS are as defined above, (vii) cyclizing a compound of the formula (II)

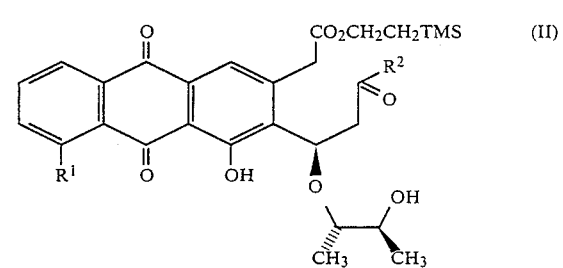

wherein R¹ is as defined above and R² is an ethyl group or an acetyl group [the compound of the formula (II) generically representing both the compound of the formula (II') and the compound of the formula (II''')] by the treatment with a base in an anhydrous organic solvent to produce a compound of the formula (I')

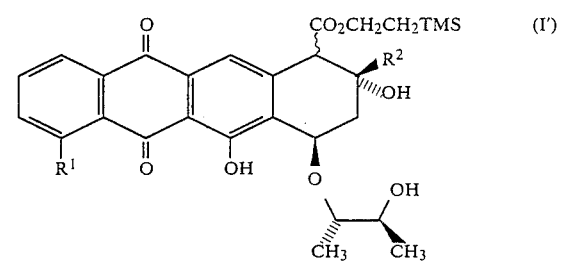

wherein R¹, R² and TMS are as defined above, and
(viii) decarboxylating the compound of the formula (I') by treating with a tetra-alkyl ammonium fluoride or hydrogen fluoride in an organic solvent to produce the desired compound of the formula (I).

12. A process of claim 11 in which the compound of the formula (II) is cyclized by treating with 1,5-diazabicyclo[4.3.0]-nonene-5 in an anhydrous organic solvent.

13. A process of claim 11 in which the compound of the formula (I') is decarboxylated by treating with tetra-n-butylammonium fluoride in an anhydrous organic solvent.

14. A compound of the formula (II)

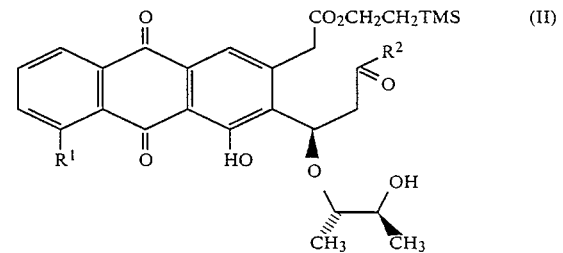

wherein R¹ is a hydrogen atom, a hydroxyl group or an alkoxyl group of 1-4 carbon atoms and R² is an ethyl group or an acetyl group.

* * * * *